(12) United States Patent
Watanabe et al.

(10) Patent No.: US 6,531,594 B2
(45) Date of Patent: Mar. 11, 2003

(54) PROCESS FOR PRODUCING 1H-3-AMINOPYRROLIDINE AND DERIVATIVES THEREOF

(75) Inventors: Michi Watanabe, Ibaraki (JP); Takeshi Nakato, Tokyo (JP); Jun Takehara, Ibaraki (JP); Kazuaki Kanno, Ibaraki (JP); Shuji Ichikawa, Ibaraki (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/933,007

(22) Filed: Aug. 21, 2001

(65) Prior Publication Data

US 2002/0042523 A1 Apr. 11, 2002

(30) Foreign Application Priority Data

Aug. 24, 2000 (JP) ........................................ 2000-253457
Feb. 13, 2001 (JP) ........................................ 2001-034853

(51) Int. Cl.$^7$ .................... C07D 477/20; C07D 471/04; C07D 207/14; C07D 207/40
(52) U.S. Cl. ........................ 540/350; 546/123; 548/546; 548/557
(58) Field of Search .......................... 548/557; 540/350; 546/123

(56) References Cited

U.S. PATENT DOCUMENTS 6,090,802 A * 7/2000 Kawamoto et al. ......... 540/350

FOREIGN PATENT DOCUMENTS

| EP | 0 218 249 | 4/1987 |
| EP | 0 302 372 | 2/1989 |
| JP | 03133954 A | * 6/1991 |
| JP | 7-506110 | 7/1995 |
| JP | 8-53412 | 2/1996 |
| WO | WO 93/22283 | 11/1993 |

OTHER PUBLICATIONS

Witiak, J Med. Chem 14(1) 24 (1971).*
J. Lee, et al., Arch. Pharm. Res., vol. 19, No. 4, pp. 312–316, "Synthesis and Anticonvulsant Evaluation of A Series of (R)– and (S)–N–Cbz–α–Aminosuccinmide and Their Structure Activity Relationship", 1996.
Patent Abstracts of Japan, JP 02 218664, Aug. 31, 1990.

* cited by examiner

Primary Examiner—Mark L Berch
(74) Attorney, Agent, or Firm—Oblon, Spivak, McClelland, Maier & Neustadt, P.C.

(57) ABSTRACT

A process for producing 1H-3-aminopyrrolidine and derivatives thereof is disclosed. The process is especially useful for producing optically active 1H-3-aminopyrrolidine and derivatives thereof and in this case comprises reacting an optically active amino-protected aspartic anhydride represented by the formula (1) with a primary amine represented by the formula R'NH$_2$, subjecting the reaction product to cyclodehydration to obtain an optically active 1-aralkyl-3-(protected amino)pyrrolidine-2,5-dione compound represented by the formula (2), subsequently eliminating the protective group from the 3-position amino group of the compound represented by the formula (2) to obtain an optically active 1-aralkyl-3-aminopyrrolidine-2,5-dione compound represented by the formula (3), reducing the carbonyl groups of the compound represented by the formula (3) to obtain either an optically active 1-aralkyl-3-aminopyrrolidine compound represented by the formula (4) or a salt thereof with a protonic acid, and then subjecting the compound represented by the formula (4) or the salt thereof to hydrogenolysis to obtain an optically active 1H-3-aminopyrrolidine or a protonic acid salt thereof.

31 Claims, No Drawings

PROCESS FOR PRODUCING 1H-3-AMINOPYRROLIDINE AND DERIVATIVES THEREOF

CROSS REFERENCES TO RELATED APPLICATIONS

This application claims priority to Japanese Patent Application No. 253457/2000, filed on Aug. 24, 2000, and to Japanese Patent Application No. 034853/2001, filed on Feb. 13, 2001, which are incorporated herein by reference in its entirety.

FIELD OF THE INVENTION

The present invention relates to a process for producing 1H-3-aminopyrrolidine and derivatives thereof, more particularly optically active 1H-3-aminopyrrolidine and derivatives thereof. More specifically, the present invention relates to an improved process for producing 1H-3-aminopyrrolidine and derivatives thereof, more particularly optically active 1H-3-aminopyrrolidine and derivatives thereof, from an aspartic acid starting material, more particularly an optically active aspartic acid starting material. The present invention also relates to methods for preparing certain antibacterial and psychotropic compounds by using the 1H-3-aminopyrrolidine and derivatives thereof prepared by such a process.

DISCUSSION OF THE BACKGROUND

Optically active 1H-3-aminopyrrolidine of the 3R or 3S configuration obtained by the invention is useful as an intermediate for various organic compounds including medicines and agricultural chemicals. In particular, the optically active compound is useful as an intermediate for antibacterial (1R,5S,6S)-6-[(1R)-1-hydroxyethyl]-1-methyl-2-[(2S,4S)-2-[(3S)-3-(L-prolyl-amino)pyrrolidin-1-ylcarbonyl]pyrrolidin-4-ylthio]-1-carbapen-2-em-3-carboxylic acid; psychotropic (S)-N-(1-benzyl-3-pyrrolidinyl)-5-chloro-4-(cyclopropylcarbonyl-amino)-2-methoxybenzamide; and the like.

Conventional processes for producing optically active 1H-3-aminopyrrolidine include (1) a method in which a racemate is optically resolved, (2) a method in which a prochiral starting material is used, and (3) a method in which the target compound is synthesized from an optically active starting material.

With respect to (1) above, known examples thereof include a process comprising subjecting racemic N-benzyl-3-aminopyrrolidine as a starting material to preferential crystallization using an optically active carboxylic acid such as, e.g., D- and L-tartaric acids, L-(+)-mandelic acid, or L-(−)-pyroglutamic acid as a resolving agent to obtain an optically active N-benzyl-3-aminopyrrolidine and then eliminating the protective group to obtain optically active 1H-3-aminopyrrolidine (see JP-A-2-218664 (the term "JP-A" as used herein means an "unexamined published Japanese patent application")) and a process in which preferential crystallization is conducted using D- and L-tartaric acid derivatives as a resolving agent to obtain optically active N-benzyl-3-aminopyrrolidine (see JP-A-9-176115). However, these processes are inefficient, for example, because: (1) the synthesis of the starting material, i.e., racemic N-benzyl-3-aminopyrrolidine, requires many steps; (2) the theoretical yield in the resolution step is 50% at the most; and (3) because many steps are necessary for the recovery and recycling of the resolving agent and the antipode.

With respect to (2) above, a process is, for example, known which comprises subjecting N-benzyl-3-pyrroline to asymmetric hydroboration to stereoselectively incorporate a hydroxyl group into the 3-position, converting the hydroxylated compound into an azide through mesylation and nucleophilic substitution, and then reducing the azide (see *J. Med. Chem.*, vol. 31, p. 1586 (1988)). However, this process is industrially disadvantageous because the N-benzyl-3-pyrroline used as a starting material and the other reagents are expensive.

With respect to (3) above, a process is, for example, known which comprises reacting optically active 1,2,4-tris(methanesulfonyl)butane obtained from an optically active 1,2,4-trisubstituted butane with benzylamine to produce 1-benzyl-3-methanesulfonoxypyrrolidine, which has one configuration in a central part of the molecule, and then subjecting it to a substitution reaction with benzylamine to produce optically active 1-benzyl-3-benzylpyrrolidine through inversion of configuration (see C. K. Ingold, Structure and Mechanism in Organic Chemistry, 2nd ed., Cornel University Press, 1969, p.519). However, this process is disadvantageous in that a technique for mass-producing the optically active 1,2,4-trisubstituted butane for use as a starting material has not been established.

On the other hand, examples of the production of optically active 1H-3-aminopyrrolidine and derivatives thereof from optically active aspartic acid include the following two processes. One known process comprises protecting the amino group of optically active aspartic acid, reducing the carboxyl groups to hydroxyl groups, protecting the hydroxyl groups to conduct cyclization, and finally eliminating the protective groups to obtain the target compound (see JP-W-7-506110, which corresponds to U.S. Pat. No. 5,177,217 (the term "JP-W" as used herein means an "unexamined published PCT application") and JP-A-8-053412). The other known process comprises adding paraformaldehyde to N-benzyloxycarbonyl-L-aspartic acid, cyclizing the acid with the aid of p-toluenesulfonic acid as a catalyst, subsequently causing the cyclized compound to add benzylamine, isolating the resultant acid amide, esterifying it with thionyl chloride and an alcohol, and then cyclizing the ester to stereoselectively produce (3S)-1-benzyl-3-benzyloxycarbonylaminopyrrolidine-2,5-dione (see *Arch. Pharm. Res.*, vol. 19(4), pp. 312–316 (1996)).

However, these processes are unsatisfactory for industrial production, for example, because they involve many reaction steps and it is difficult to purify or isolate the compound produced in each step.

Also known is a process for stereoselectively producing (3S)-1-benzyl-3-benzyloxycarbonylamino-pyrrolidine-2,5-dione (succinimide compound) which comprises converting N-benzyloxycarbonyl-L-aspartic acid into its anhydride, causing the anhydride to add benzylamine, isolating the resultant acid amide, and cyclizing it with acetic anhydride (see JP-A-1-110626, which corresponds to EP 0 302 372). However, an investigation made by the present inventors revealed that racemization occurs in the step of succinimide synthesis in this process (see, Comparative Example 1 below). Furthermore, this process cannot be regarded as industrially advantageous because lithium aluminum hydride, which is used in the subsequent step of reducing the succinimide compound (Comparative Example 2), is expensive.

SUMMARY OF THE INVENTION

Accordingly it is one object of the invention to provide a novel process for producing 1H-3-aminopyrrolidine and derivatives thereof.

It is another object of the present invention to provide a novel process for producing optically active 1H-3-aminopyrrolidine and derivatives thereof.

It is another object of the present invention to provide a novel process for producing 1H-3-aminopyrrolidine and derivatives thereof from an aspartic acid starting material.

It is another object of the present invention to provide a novel process for producing optically active 1H-3-aminopyrrolidine and derivatives thereof from an optically active aspartic acid starting material.

It is another object of the present invention to provide an industrially advantageous process for safely producing high-quality optically active 1H-3-aminopyrrolidine and derivatives thereof at low cost from optically active aspartic acid.

It is another object of the present invention to provide a novel process for preparing 1-aralkyl-3-(protected amino) pyrrolidine-2,5-dione compounds (succinimide compounds), which are useful as intermediates in such a process.

It is another object of the present invention to provide novel processes for preparing certain antimicrobial drugs by using the 1H-3-aminopyrrolidine and derivatives thereof prepared by such a process.

It is another object of the present invention to provide novel processes for preparing certain psychotic by using the 1H-3-aminopyrrolidine and derivatives thereof prepared by such a process.

These and other objects which will become apparent during the following detailed description, have been achieved by the inventors' discovery that an optically active 1-aralkyl-3-(protected amino)pyrrolidine-2,5-dione compound (succinimide compound) can be produced, while avoiding a decrease in optical purity, by reacting an optically active amino-protected aspartic anhydride with a primary amine in an organic solvent and then subjecting the reaction product to cyclodehydration in the presence of an acid catalyst. The present inventors have further found that when the succinimide compound obtained is subjected to elimination of the protective group therefrom and then reduced with a reducing agent prepared by adding dimethyl sulfate or aluminum chloride to sodium boron hydride, then a 3-aminopyrrolidine compound having a high chemical purity and a high optical purity can be obtained. The inventors have furthermore found that either an optically active 1H-3-aminopyrrolidine compound retaining the configuration at the 3-position of the pyrrolidine ring or a salt thereof with a protonic acid can be produced in high yield by subjecting the 3-aminopyrrolidine compound or a protonic acid salt thereof to hydrogenolysis. The invention has been achieved based on these findings.

Thus, in a first embodiment, the present invention provides:

1. A process for producing 1H-3-aminopyrrolidine or a protonic acid salt thereof, which comprises:

(a) reacting an amino-protected aspartic anhydride of formula (1):

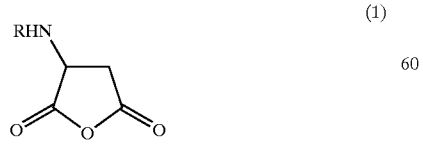

(1)

wherein R represents a benzyloxycarbonyl group which may have one or more substituents on the benzene ring, with a primary amine represented by the formula R'NH$_2$ wherein R' represents an aralkyl group which may have one or more substituents on the aromatic ring, to obtain a reaction product;

(b) subjecting said reaction product to cyclodehydration to obtain a 1-aralkyl-3-(protected amino)pyrrolidine-2, 5-dione compound of formula (2):

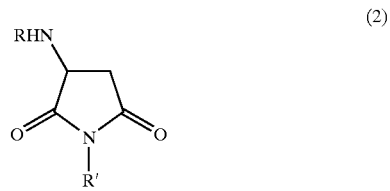

(2)

wherein R has the same meaning as in formula (1) and R' is as defined above;

(c) replacing R with a hydrogen at the 3-position amino group of the compound of formula (2) to obtain a 1-aralkyl-3-aminopyrrolidine-2,5-dione compound of formula (3):

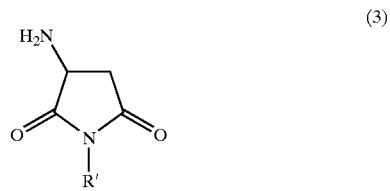

(3)

wherein R' has the same meaning as in formula (2);

(d) reducing the carbonyl groups of the compound of formula (3) to obtain either a 1-aralkyl-3-aminopyrrolidine compound of formula (4):

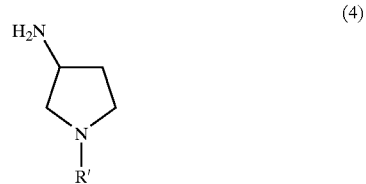

(4)

wherein R' has the same meaning as in formula (2), or a salt thereof with a protonic acid; and (e) subjecting said compound of formula (4) or said salt thereof to hydrogenolysis to obtain 1H-3-aminopyrrolidine or a protonic acid salt thereof.

In a second embodiment, the present invention provides:

2. A process for producing optically active 1H-3-aminopyrrolidine or a protonic acid salt thereof, which comprises:

(a) reacting an optically active amino-protected aspartic anhydride of formula (1') or (1"):

(1')

or

-continued

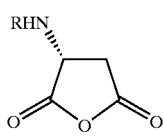
(1″)

wherein R represents a benzyloxycarbonyl group which may have one or more substituents on the benzene ring, with a primary amine represented by the formula R'NH₂ wherein R' represents an aralkyl group which may have one or more substituents on the aromatic ring, to obtain a reaction product;

(b) subjecting said reaction product to cyclodehydration to obtain an optically active 1-aralkyl-3-(protected amino)pyrrolidine-2,5-dione compound of formula (2') or (2″):

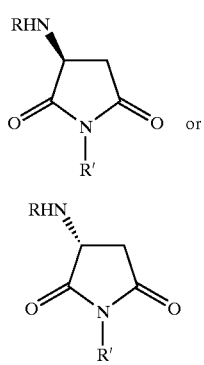
(2')

(2″)

wherein R has the same meaning as in formula (1') or (1″) and R' is as defined above;

(c) replacing R with a hydrogen at the 3-position amino group of the compound of formula (2') or (2″) to obtain an optically active 1-aralkyl-3-aminopyrrolidine-2,5-dione compound of following formula (3') or (3″):

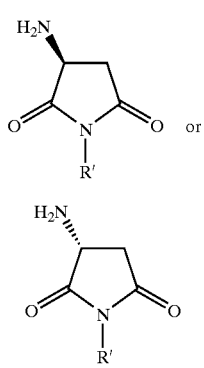
(3')

(3″)

wherein R' has the same meaning as in formula (2') or (2″);

(d) reducing said compound represented by formula (3') or (3″) to obtain either an optically active 1-aralkyl-3-aminopyrrolidine compound of formula (4') or (4″):

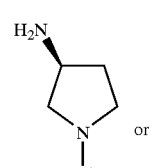
(4')

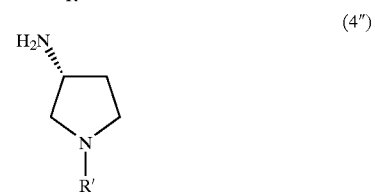
(4″)

wherein R' has the same meaning as in formula (2') or (2″), or a salt thereof with a protonic acid; and (e) subjecting the compound of formula (4') or (4″) or said salt thereof to hydrogenolysis to obtain optically active 1H-3-aminopyrrolidine or a protonic acid salt thereof.

In a third embodiment, the present invention provides:

3. A process for producing optically active 1H-3-aminopyrrolidine or a protonic acid salt thereof, which comprises:

(a) a step for obtaining a reaction product of an optically active amino-protected aspartic anhydride of formula (1') or (1″):

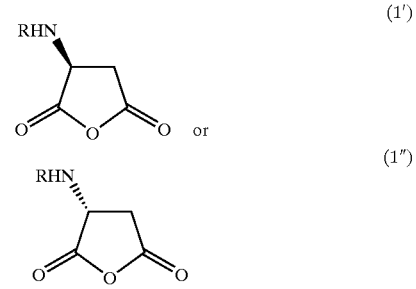
(1')

(1″)

wherein R represents a benzyloxycarbonyl group which may have one or more substituents on the benzene ring, with a primary amine represented by the formula R'NH₂ wherein R' represents an aralkyl group which may have one or more substituents on the aromatic ring;

(b) a step for converting said reaction product to an optically active 1-aralkyl-3-(protected amino) pyrrolidine-2,5-dione compound of formula (2') or (2″):

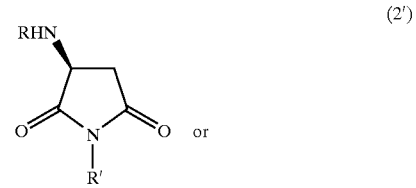
(2')

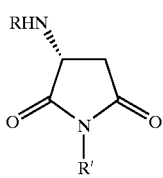
(2″)

wherein R has the same meaning as in formula (1') or (1″) and R' is as defined above;

(c) a step for converting the compound represented by formula (2') or (2″) to an optically active 1-aralkyl-3-aminopyrrolidine-2,5-dione compound of formula (3') or (3″):

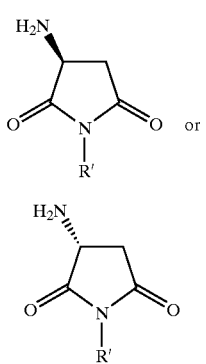
(3')

(3″)

wherein R' has the same meaning as in formula (2') or (2″);

(d) a step for converting the compound of formula (3') or (3″) to either an optically active 1-aralkyl-3-aminopyrrolidine compound of formula (4') or (4″):

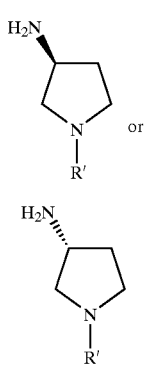
(4')

(4″)

wherein R' has the same meaning as in formula (2') or (2″), or a salt thereof with a protonic acid; and (e) a step for converting the compound of formula (4') or (4″) or said salt thereof to hydrogenolysis to obtain optically active 1H-3-aminopyrrolidine or a protonic acid salt thereof.

In a fourth embodiment, the present invention provides:

4. A process for producing an optically active 1-aralkyl-3-(protected amino)pyrrolidine-2,5-dione compound of formula (2') or (2″):

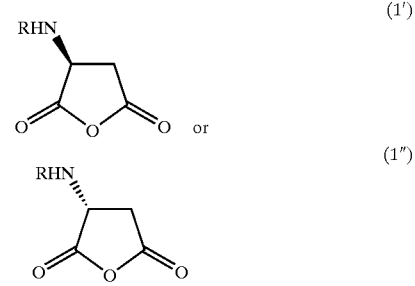
(2')

(2″)

wherein R represents a benzyloxycarbonyl group which may have one or more substituents on the benzene ring; and R' represents an aralkyl group which may have one or more substituents on the aromatic ring, which process comprises:

(a) reacting an optically active amino-protected aspartic anhydride of formula (1') or (1″):

(1')

(1″)

with a primary amine of the formula R'NH$_2$ wherein R and R' are as defined above, to obtain a reaction product; and (b) subjecting said reaction product to cyclodehydration in the presence of an acid catalyst.

In a fifth embodiment, the present invention provides:

5. A process for producing an optically active 1-aralkyl-3-(protected amino)pyrrolidine-2,5-dione compound of formula (2') or (2″):

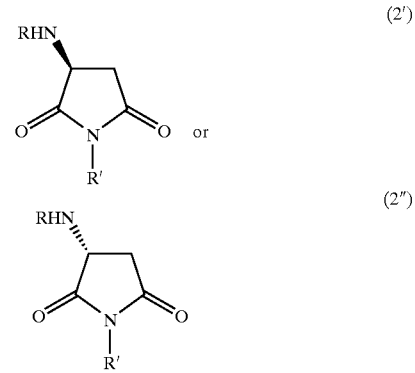
(2')

(2″)

wherein R represents a benzyloxycarbonyl group which may have one or more substituents on the benzene ring; and R' represents an aralkyl group which may have one or more substituents on the aromatic ring, which process comprises:
(a) dehydrating an optically active amino-protected aspartic acid of formula (B) or (B'):

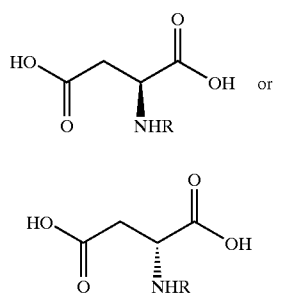

wherein R has the same meaning as in formula (2') or (2"), to obtain an optically active amino-protected aspartic anhydride;
(b) reacting said anhydride with a primary amine of the formula R'NH$_2$ wherein R' represents an aralkyl group which may have one or more substituents on the aromatic ring, to obtain a reaction product; and
(c) subjecting said reaction product to cyclodehydration, wherein said reacting said anhydride and said subjecting said reaction product are carried out in a same reactor without removing said reaction product from said reactor between said reacting said anhydride and said subjecting said reaction product.

In a sixth embodiment, the present invention provides:

6. A process for producing optically active 1H-3-aminopyrrolidine or a protonic acid salt thereof, which process comprises:
(a) subjecting a compound of formula (4') or (4"):

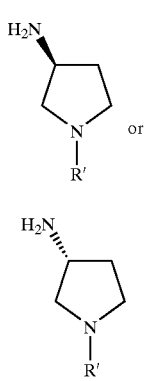

wherein R' represents an aralkyl group which may have one or more substituents on the aromatic ring, or a salt thereof with a protonic acid, to hydrogenolysis to obtain said optically active 1H-3-aminopyrrolidine or a protonic acid salt thereof.

In a seventh embodiment, the present invention provides:

7. A process for producing an optically active 1-aralkyl-3-aminopyrrolidine compound of formula (4') or (4"):

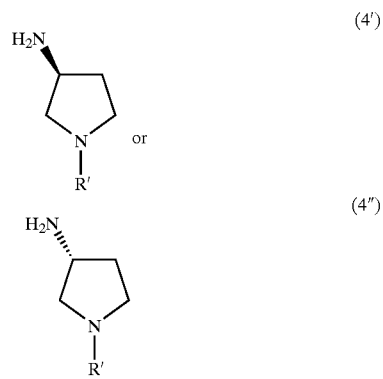

wherein R' represents an aralkyl group which may have one or more substituents on the aromatic ring, or a salt thereof with a protonic acid,
which process comprises:
(a) reducing an optically active 1-aralkyl-3-aminopyrrolidine-2,5-dione compound of formula (3') or (3"):

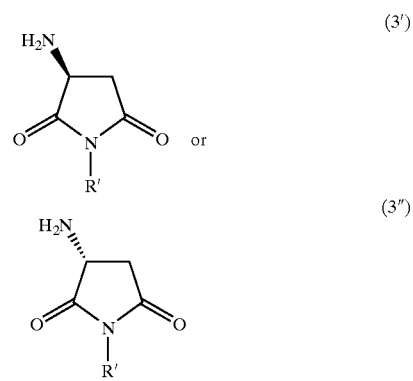

wherein R' has the same meaning as in formula (4); with a reducing agent prepared by adding dimethyl sulfate or aluminum chloride to sodium boron hydride.

In a eighth embodiment, the present invention provides:
8. A process for producing a 1-methyl-carbapenem derivative represented by the following formula (I):

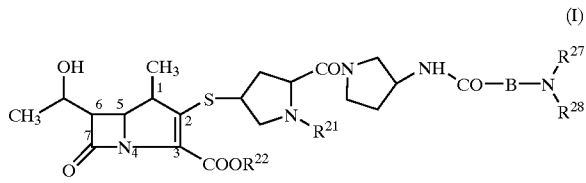

wherein $R^{21}$ represents a hydrogen or methyl group; $R^{22}$ represents hydrogen or an ester residue which is hydrolyzable in vivo; $R^{27}$ represents hydrogen, methyl or ethyl; B represents 1,4-diphenylene, 1,4-cyclohexylenemethyl, methylene, methyl ethylene, ethylene, trimethylene, or 2-hydroxypropylene; $R^{28}$ represents formimidoyl, acetoimidoyl, or amidino; or the group —B—NR$^{27}$R$^{28}$ represents a 5 or 6 membered cyclic group,
which process comprises converting 1H-3-aminopyrrolidine or a protonic acid salt thereof to said compound of formula (I), the improvement being said 1H-3-aminopyrrolidine or a protonic acid salt thereof is produced by the present process.

In a ninth embodiment, the present invention provides:

9. A process for producing a N-(3-pyrolidynyl) benzamido derivative represented by the following formula (II):

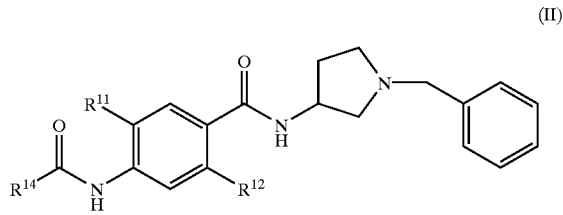

(II)

wherein $R^{11}$ represents a halogen atom; $R^{12}$ represents an alkoxy group having from 1 to 3 carbon atoms; $R^{14}$ represents a hydrocarbon ring group having from 3 to 6 carbon atoms which may be unsubstituted or substituted by halogen atom, which comprises converting a compound of formula (4') or (4")or protonic acid salt thereof to said compound of formula (II), the improvement being said compound of formula (4') or (4") or protonic acid salt thereof is produced by the present process.

In a tenth embodiment, the present invention provides:

10. A method for producing a compound of formula (III):

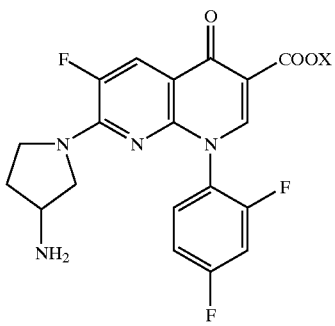

(III)

wherein X is hydrogen or a carboxy protecting group and pharmaceutically acceptable salts thereof, which comprises converting the compound of formula (4') or (4") produced by the present invention to said compound of formula (III).

Thus, according to the present invention, a high-quality optically active 1H-3-aminopyrrolidine compound can be industrially advantageously produced safely at low cost from an optically active aspartic acid.

DETAILED DESCRIPTION OF THE PREFERRED EMBODIMENTS

In the process of the present invention, aspartic acid is used as the starting material. In the detailed description which follows, the present methods will be discussed in the context of the use of an optically active aspartic acid as the starting material for the production of optically active 1H-3-aminopyrrolidine and derivatives thereof. However, it is to be understood that the present methods may be likewise carried out starting with aspartic acid which is not optically active or is not a single pure enantiomer. In fact, although the following detailed description describes the use of a staring material obtained from L-aspartic acid, it should be recognized that the present processes could instead use D-aspartic acid as the starting material. It should also be understood that the degree of optical activity exhibited by the 1H-3-aminopyrrolidine compounds produced from the present process will depend to some extent on the degree of optical activity exhibited by the aspartic acid used as the starting material. However, it is preferred that the 1H-3-aminopyrrolidine and derivatives thereof produced by the present process exhibit an optical activity which is at least 50% ee, preferably at least 75% ee, more preferably at least 90% ee, even more preferably at least 95%, even more preferably at least 99% ee, where the term "ee" refers to the enantiomeric excess of the product. It is also especially preferred that the asymmetirc carbon atom at the 3 position of the pyrrolidine ring in the 1H-3-aminopyrrolidine and derivatives thereof produced by the present process have the same absolute configuartion as the alpha carbon in L-aspartic acid.

In the context of the present invention, it is to be understood that the formula (4):

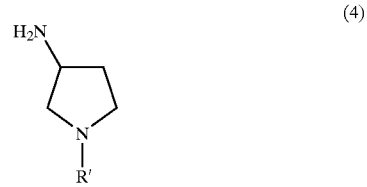

(4)

indicates that the stereochemistry at the 3-position of the pyrrolidine ring is unspecified. That is, formula (4) encompasses all compounds of that formula regardless of the stereochemistry at the 3-position of the pyrrolidine ring and includes the racemate, the pure L enantiomer, the pure D enantiomer, and all degrees of enantiomeric excess between the racemic mixture and either the L enantiomer or the D enantiomer.

It should also to be understood that the formula (4'):

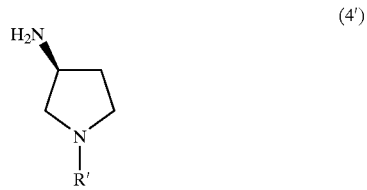

(4')

indicates that the stereochemistry at the 3-position of the pyrrolidine ring is of the configuration. That is, formula (4') encompasses not only the pure S-enantiomer, but also all compounds of that formula so long as there is an enantiomeric excess of the shown enantiomer.

It should also to be understood that the formula (4"):

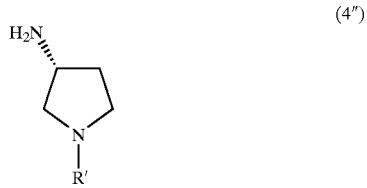

(4")

indicates that the stereochemistry at the 3-position of the pyrrolidine ring is of the R configuration. That is, formula (4") encompasses not only the pure R-enatiomer, bit also all compounds of that formula so long as there is an enantiomeric excess of the shown enantiomer.

The present processes will now be described in detail in the context of using optically active aspartic acid as a starting material to produce optically active 1H-3-aminopyrrolidine and derivatives thereof. The steps of the process of the invention are shown in the following scheme I.

Examples of the substituents which the benzene ring may have include alkoxy groups having 1 to 3 carbon atoms, such as methoxy, ethoxy, and propoxy; halogen atoms such as fluorine, chlorine, and bromine atoms; and nitro.

Specific examples of the substituent R include benzyloxycarbonyl, 4-bromobenzyloxycarbony, 2,4-dichlorobenzyloxycarbonyl, 4-nitrobenzyloxycarbonyl, 2-nitrobenzyloxycarbonyl, 4-methoxybenzyloxycarbonyl,

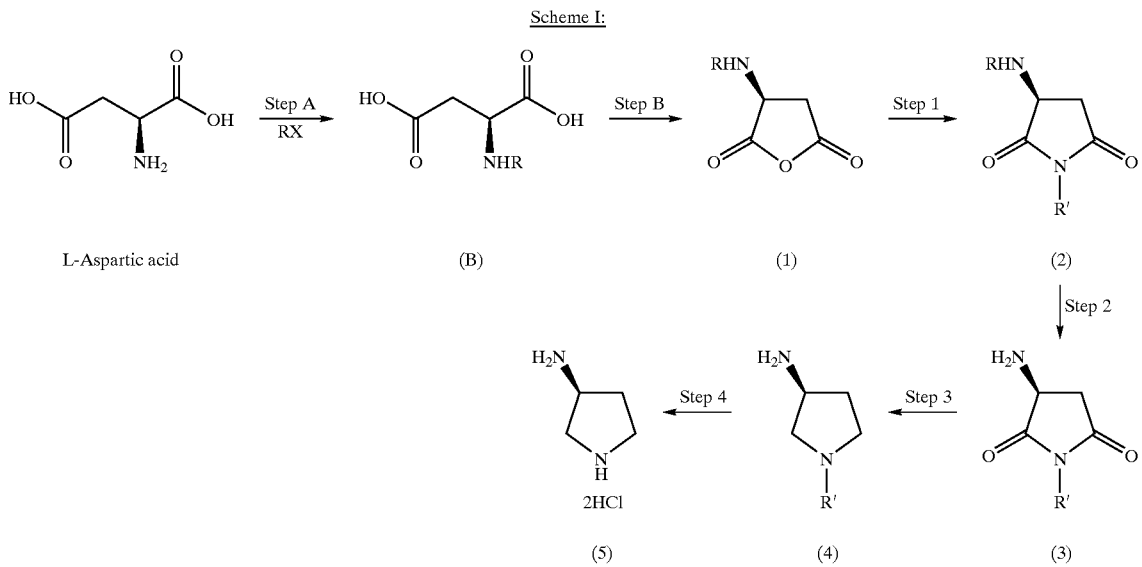

Scheme I:

Production of Optically Active Amino-protected Aspartic Acid (Step A)

The optically active amino-protected aspartic acid to be used may be a commercially available one, or may be synthesized from an optically active aspartic acid. For example, (3S)-N-benzyloxycarbonylaminoaspartic acid can be produced by reacting a commercial product of optically active aspartic acid with benzyloxycarbonyl chloride in the presence of a base (see, for example, JP-A-64-63565, JP-A-60-190754, JP-A-60-185755, JP-A-60-136550, JP-A-57-14570, and JP-A-56-110661, all of which are incorporated herein by reference in their entirety). In formula (B), R has the same meaning as in formula (1), and the remaining compounds of formula (B) may also be prepared by appropriate variation of the reagents and conditions described in JP-A-64-63565, JP-A-60-190754, JP-A-60-185755, JP-A-60-136550, JP-A-57-14570, and JP-A-56-110661.

Production of Optically Active 3-(Protected Amino) pyrrolidine-2,5-dione Compound (Step B and Step 1)

The optically active amino-protected aspartic acid (B) is subjected to a dehydration reaction to thereby obtain an optically active amino-protected aspartic anhydride represented by the following formula (1):

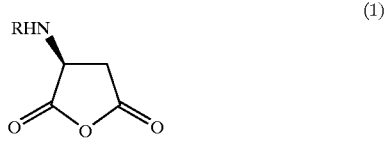

(1)

wherein R represents a benzyloxycarbonyl group which many have one or more substituents on the benzene ring. Specifically, this reaction is accomplished by heating the acid together with a dehydrating agent in an organic solvent or without using a solvent.

and 3,5-dimethoxybenzyloxycarbonyl. Preferred of these are benzyloxycarbonyl and 4-bromobenzyloxycarbonyl.

Examples of the organic solvent include lower-alkyl esters of lower fatty acids, such as ethyl acetate, propyl acetate, and butyl acetate, aliphatic hydrocarbons such as hexane, heptane, and octane, and aromatic hydrocarbons such as benzene, toluene, and xylene. Preferred of these are lower-alkyl esters of lower fatty acids. More preferred is ethyl acetate.

Examples of the dehydrating agent include lower fatty acid anhydrides such as acetic anhydride and trifluoroacetic anhydride, lower fatty acid chlorides such as acetyl chloride and propionyl chloride, and halogenating agents such as thionyl chloride. More preferred are lower fatty acid chlorides.

This step will now be described in detail in the context of the production of N-benzyloxycarbonyl-L-aspartic anhydride. However, it is to be understood that the other compounds of formula (1) may be produced by variation of the conditions set forth below and that the selection of the appropriate conditions for the production of any compound of formula (1) from those set out below is within the skill of one skilled in the art.

In the case where N-benzyloxycarbonyl-L-aspartic anhydride, for example, is produced as the compound represented by formula (1), acetyl chloride is used as the dehydrating agent in an amount of generally at least 1.0 mol, preferably at least 1.2 mol, per mol of the (3S)-N-benzyloxycarbonylaminoaspartic acid. The reaction is conducted at a temperature of generally from 10 to 100° C., preferably from 30 to 60° C. Although the reaction time varies depending on the temperature, the reaction substantially terminates usually in 1 to 5 hours. It is preferred to conduct the reaction with stirring in an inert gas stream, e.g., nitrogen, in order to remove the hydrogen chloride being yielded. After completion of the reaction, the solvent and the excess acetyl chloride are distilled off under reduced pressure. A poor solvent is added to the residue to crystallize the reaction product. As the poor solvent may be used an aromatic hydrocarbon such as toluene or xylene, or an aliphatic hydrocarbon such as hexane, heptane, or octane, or the like. The crystals formed are isolated by filtration and vacuum-dried to obtain an optically active amino-protected aspartic anhydride.

The optically active amino-protected aspartic anhydride obtained by the method described above is reacted with a primary amine represented by the formula R'NH$_2$, wherein R' represents an aralkyl group which may have one or more substituents on the aromatic ring, preferably in the presence of an organic solvent. Thereafter, the reaction product is subjected to cyclodehydration preferably in the presence of an acid catalyst. Thus, an optically active 1-aralkyl-3-(protected amino)pyrrolidine-2,5-dione compound is produced which is represented by the following formula (2):

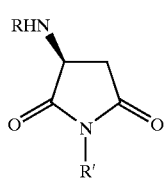

(2)

wherein R has the same meaning as in formula (1) and R' is as defined above.

Examples of the substituents which the aromatic ring of the primary amine R'NH$_2$ may have include alkoxy groups having 1 to 3 carbon atoms, such as methoxy, ethoxy, and propoxy; halogen atoms such as fluorine, chlorine, and bromine atoms; and nitro.

Specific examples of this primary amine include benzylamine, 2-bromobenzylamine, 3-bromobenzylamine, 4-bromobenzylamine, 2,4-dichlorobenzylamine, 2,6-dichlorobenzylamine, 3,4-dichlorobenzylamine, 2-nitrobenzylamine, 3-nitrobenzylamine, and 4-nitrobenzylamine. Preferred of these is benzylamine. Especially in the case where (3S)-1-benzyl-3-(carbobenzyloxyamino)pyrrolidine-2,5-dione is produced as an example of the optically active compound represented by formula (2), benzylamine is used as the primary amine.

Suitable examples of the reaction solvent include aromatic hydrocarbons such as benzene, toluene, and xylene; aliphatic hydrocarbons such as hexane, heptane, and octane; ethers such as diisopropyl ether and dimethoxyethane; and mixed solvents comprising one or more of these. Preferred of these is toluene. It is more preferred to use a mixed solvent comprising a polar solvent, e.g., dimethylformamide, dimethylacetamide, dimethyl sulfoxide, or a polyethylene glycol dialkyl ether, and toluene. The proportion of the polar solvent is generally from 1 to 20% by volume, preferably from 5 to 10% by volume, based on the toluene.

Examples of the acid catalyst include protonic acids such as sulfuric acid, phosphoric acid, and p-toluenesulfonic acid; and Lewis acids such as aluminum chloride and zinc chloride. Preferred of these is p-toluenesulfonic acid. The acid catalyst is used in an amount of generally from 0.1 to 50% by mole, preferably from 1 to 20% by mole, based on the moles of (N-carbobenzyloxy)aspartic anhydride.

From the standpoint of preventing the optical purity from decreasing, the reaction temperature is generally from 60 to 150° C., preferably from 80 to 120° C., although it varies depending on the boiling point of the solvent used. It is preferable that the water being created by the dehydration be continuously discharged from the system by azeotropy.

After completion of the reaction, the solvent is removed by distillation, and a solvent in which the reaction product is readily soluble, such as, e.g., an acetic acid ester, is added to the residue. This solution is washed successively with an aqueous acid solution and an aqueous alkali solution. Finally, the solvent is removed by distillation. Thus, a compound represented by formula (2) having a high optical purity and a high chemical purity is obtained. In particular, an example of this optically active compound is (3S)-1-benzyl-3-(carbobenzyloxyamino)pyrrolidine-2,5-dione.

In the case where an organic solvent comprising an aromatic hydrocarbon was used as the reaction solvent, purification by crystallization after completion of the reaction can be conducted without the necessity of solvent removal by distillation. Specifically, the purification can be conducted in the following manner. After completion of the reaction, the reaction mixture is washed with an aqueous alkali solution and then with a saturated aqueous sodium chloride solution while being kept at 70° C. or higher, subsequently heated and refluxed to conduct azeotropic dehydration, and then cooled to cause crystallization. Crystals begin to precipitate at around 65° C., and this mixture is further stirred at 20° C. Thus, optically active (3 S)-1-benzyl-3-benzyloxycarbonyl-aminopyrrolidine-2,5-dione purified to a higher optical purity can be obtained.

Toluene is preferred as the aromatic hydrocarbon. A mixed solvent comprising an aromatic hydrocarbon and an aliphatic hydrocarbon such as hexane, heptane, or octane may be used.

It is also possible to use a technique in which after an optically active amino-protected aspartic anhydride is synthesized from an optically active amino-protected aspartic acid, an optically active 1-aralkyl-3-(protected amino) pyrrolidine-2,5-dione compound is synthesized from the anhydride in the same reactor without removing the anhydride from the reactor. Specifically, this method comprises synthesizing an optically active amino-protected aspartic anhydride in the same manner as described above, subsequently replacing the reaction solvent, and subjecting the acid anhydride to reaction with a primary amine R'NH$_2$ and then to cyclodehydration according to the method described above. Thus, the target optically active 1-aralkyl-3-(protected amino)pyrrolidine-2,5-dione compound can be synthesized.

From the optically active 3-(protected amino)pyrrolidine-2,5-dione compound represented by formula (2) can be produced a compound useful as an intermediate for various organic compounds including medicines and agricultural chemicals.

Production of Optically Active 1-Aralkyl-3-aminopyrrolidine-2,5-dione (Step 2)

An optically active 1-aralkyl-3-aminopyrrolidine-2,5-dione compound represented by the following formula (3):

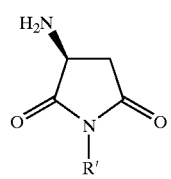

(3)

wherein R' has the same meaning as in formula (2), can be produced by eliminating the protective group from the 3-position amino group of the optically active 1-aralkyl-3-(protected amino)pyrrolidine-2,5-dione compound.

Specifically, the compound represented by formula (2) is catalytically reduced in a hydrogen atmosphere using a metallic catalyst, e.g., Pd/C, to eliminate the protective group from the 3-position amino group to obtain the target compound. This step will now be described in detail in the context of the production (3S)-3-amino-1-benzylpyrrolidine-2,5-dione. However, it is to be understood that the other compounds of formula (3) may be produced by variation of the conditions set forth below and that the selection of the appropriate conditions for the production of any compound of formula (3) from those set out below is within the skill of one skilled in the art.

In the case where (3S)-3-amino-1-benzylpyrrolidine-2,5-dione is produced, the reaction is conducted in a solvent such as, e.g., water, methanol, ethanol, isopropyl alcohol, or 1,2-dimethoxyethane using 5% or 10% Pd/C as a catalyst in an amount of from 0.1 to 1.0% by mole, preferably from 0.2 to 0.5% by mole, based on the moles of (3S)-1-benzyl-3-benzyloxycarbonylaminopyrrolidine-2,5-dione. This reaction proceeds at a temperature of from 20 to 150° C. and a pressure of from ordinary pressure to 30 kg/cm². A preferred range of the pressure is from ordinary pressure to 5 kg/cm². Usually, the reaction is completed in 2 to 30 hours.

In the case where 1,2-dimethoxyethane is to be used as a solvent in the subsequent step, use of 1,2-dimethoxyethane as a solvent in this reaction for protective-group elimination is advantageous in that the reaction mixture obtained through this reaction can be subjected to the subsequent step without isolating the reaction product and that the only act necessary therefor is to remove the catalyst by filtration.

Method 1 for Producing Optically Active 1-Aralkyl-3-aminopyrrolidine Compound (Step 3)

An optically active 1-aralkyl-3-aminopyrrolidine compound represented by the following formula (4):

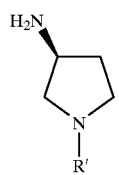

(4)

wherein R' has the same meaning as in formula (2), can be produced by reducing the carbonyl groups of the optically active 1-aralkyl-3-aminopyrrolidine-2,5-dione compound.

Specifically, a reducing agent prepared by adding dimethyl sulfate to sodium boron hydride is used for the reduction.

In the case where optically active (3S)-3-amino-1-benzylpyrrolidine is produced, the amount of sodium boron hydride to be used is generally from 1 to 7 mol, preferably from 4 to 7 mol, per mol of the optically active (3S)-3-amino-1-benzylpyrrolidine-2,5-dione used as a substrate. Dimethyl sulfate is used in the same molar amount as the sodium boron hydride.

The reduction is conducted in an inert organic solvent. Examples of the inert organic solvent include open chain ethers such as diethyl ether, methyl t-butyl ether, di-n-butyl ether, dimethoxyethane, diethylene glycol dimethyl ether, and diethylene glycol diethyl ether; cyclic ethers such as tetrahydrofuran and dioxane; hydrocarbons such as toluene, xylene, and tetralin; and mixed solvents composed of two or more thereof. It is preferred to use a cyclic ether, especially tetrahydrofuran.

Dimethyl sulfate is added dropwise to a tetrahydrofuran solution of sodium boron hydride at −10 to 10° C., and this mixture is stirred at a temperature of from 0 to 20° C. for from 5 to 10 hours. Subsequently, a tetrahydrofuran solution of the substrate is added thereto at −10 to 10° C. and the reaction mixture is stirred. The reaction temperature is generally from 0 to 100° C. preferably from room temperature to 50° C. Although the reaction is conducted until substantially all the substrate disappears, the time required therefor varies depending on the reaction temperature. For example, the reaction is completed in 10 hours at 25° C. and in 6 hours at 50° C. By keeping the reaction temperature at 30° C., or lower during the reduction, optical purity can be inhibited from decreasing. After completion of the reaction, water or methanol is added to the reaction mixture to decompose the excess reducing agent. The reaction mixture is concentrated, subsequently acidified with hydrochloric acid or the like, and then stirred for several hours. Thereafter, the aqueous layer is alkalified with caustic soda or the like and then extracted with an organic solvent. Thus, optically active (3S)-3-amino-1-benzylpyrrolidine having a high optical purity and a high chemical purity can be obtained.

Method 2 for Producing Optically Active 1-Aralkyl-3-aminopyrrolidine Compound (Step 3)

An optically active 1-aralkyl-3-aminopyrrolidine compound can be produced also by a method in which a reducing agent prepared by adding aluminum chloride to sodium boron hydride is used. In this method, the amount of sodium boron hydride to be used can be reduced as compared with the case of using a reducing agent prepared by adding dimethyl sulfate.

In the case where optically active (3 S)-3-amino-1-benzylpyrrolidine is produced, the amount of sodium boron hydride to be used is generally from 1 to 7 mol, preferably from 2 to 5 mol, per mol of the optically active (3S)-3-amino-1-benzylpyrrolidine-2,5-dione used as a substrate. Aluminum chloride is used in an amount of generally from 0.1 to 1 mol, preferably 0.33 mol, per mol of the sodium boron hydride.

The reduction is conducted in an inert organic solvent. Examples of the inert organic solvent include open chain ethers such as diethyl ether, methyl t-butyl ether, di-n-butyl ether, dimethoxyethane, diethylene glycol dimethyl ether, and diethylene glycol diethyl ether; cyclic ethers such as tetrahydrofuran and dioxane; hydrocarbons such as toluene, xylene, and tetralin; and mixed solvents composed of two or more thereof. It is preferred to use an open chain ether, especially 1,2-dimethoxyethane.

Aluminum chloride is added dropwise to a 1,2-dimethoxyethane solution of sodium boron hydride at 0 to 10° C., and this mixture is stirred at a temperature of from 0 to 50° C. for from 1 to 5 hours. Subsequently, a dimethoxyethane solution of the substrate is added thereto at 0 to 10° C. and the reaction mixture is stirred. The reaction temperature is generally from 0 to 100° C., preferably from room temperature to 50° C. Although the reaction is conducted until substantially all the substrate disappears, the time required therefor varies depending on the reaction temperature. For example, the reaction is completed in 12 hours at 25° C. By keeping the reaction temperature at 30° C. or lower during the reduction, optical purity can be inhibited from decreasing. After completion of the reaction, water or methanol is added to the reaction mixture to decompose the excess reducing agent. The reaction mixture is concentrated, subsequently acidified with hydrochloric acid or the like, and then stirred for several hours. Thereafter, the aqueous layer is alkalified with caustic soda or the like and then extracted with an organic solvent. Thus, optically active (3S)-3-amino-1-benzylpyrrolidine having a high optical purity and a high chemical purity can be obtained.

Production of Optically Active 1H-3-Aminopyrrolidine Compound (Step 4)

An optically active 1H-3-aminopyrrolidine compound or a salt thereof with a protonic acid can be produced by subjecting the optically active 1-aralkyl-3-amino-pyrrolidine compound or a salt thereof to hydrogenolysis. Specifically, the compound represented by formula (4) or a salt thereof is catalytically reduced in a hydrogen atmosphere using a metallic catalyst, e.g., Pd/C, to eliminate the 1-position protective group and thereby obtain the target compound.

For example, in the case where (3S)-1H-3-aminopyrrolidine dihydrochloride is produced, solvents such as water, methanol, ethanol, and isopropyl alcohol are used alone or as a mixture of two or more thereof in an autoclave to conduct the reaction preferably in the pressure of an acid such as acetic acid or hydrochloric acid. The addition of an acid can heighten the rate of reaction. The acid is added in an amount of generally from 1.0 to 5.0 mol, preferably from 1.0 to 2.0 mol, per mol of the (3S)-3-amino-1-benzylpyrrolidine.

As the catalyst is, for example, used Pd/C in an amount of generally from 0.25 to 5.0% by mole, preferably from 1.0 to 3.0% by mole, based on the (3S)-3-amino-1-benzylpyrrolidine. This reaction proceeds at a temperature of from 20 to 150° C. in a hydrogen atmosphere having a pressure of generally from ordinary pressure to 30 kg/cm², preferably from ordinary pressure to 10 kg/cm², more preferably from ordinary pressure to 5 kg/cm2. The reaction is completed usually in 2 to 30 hours. After completion of the reaction, the catalyst is removed by filtration, and hydrogen chloride or hydrochloric acid is added to the filtrate to cause crystallization. The crude crystals are taken out by filtration and then recrystallized. Thus, (3S)-1H-3-aminopyrrolidine dihydro-chloride having a high chemical purity and a high optical purity is obtained.

As noted above, the optically active aminopylrrolidine compounds produced by the present method are useful for producing 1-methyl-carbapenem derivatives represented by the following formula (I):

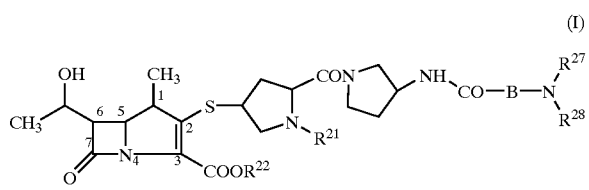

wherein $R^{21}$ represents a hydrogen or methyl group; $R^{22}$ represents hydrogen or an ester residue which is hydrolyzable in vivo; $R^{27}$ represents hydrogen, methyl or ethyl; B represents 1,4-diphenylene, 1,4-cyclohexylenemethyl, methylene, methyl ethylene, ethylene, trimethylene, or 2-hydroxypropylene; $R^{28}$ represents formimidoyl, acetoimidoyl, or amidino; or the group —B—$NR^{27}R^{28}$ represents a 5 or 6 membered cyclic group, which are useful as an antibacterial agents.

In the compounds of formula (I), suitable ester residues which are subject to hydrolysis in vivo, include acyloxyalkyl groups, such as pivaloyloxymethyl, acetoxymethyl, and 1-methylcyclohexylcarbonyloxymethyl; alkoxy carbonyloxyalkyl groups, such as 1-(isopropoxycarbonyloxy) ethyl and 1-(cyclohexylcarbonyloxy) ethyl; and 1-(2-oxo-1,3-dioxolene-4-yl) alkyl groups, which may have an alkyl or allyl group on the 5-position, such as 5-methyl-2-oxo-1,3-dioxolene-4-ylmethyl.

The 1H-3-aminopyrrolidine produced by the present processes may be converted to the compounds of formula (I) by the methods described in Japanese Patent No. 2955276, which is incorporated herein by reference in its entirety. As an example of the method of producing the above mentioned 1-methyl-carbapenem derivatives, the reaction for producing (1R,5S,6S)-6-[(1R)-1-hydroxyethyl]-1-methyl-2-[(2S,4S)-2-[(3S)-3-(L-pyrrolidin-1-ylcarbonyl]pyrrolidin-4-ylthio]-1-carbapen-2-em-3-carboxylic acid (14) by using an optical active amino pyrrolidine compound is described in reaction scheme II. However, it is to be understood that the remaining compounds of formula (I) may be prepared by varying the specific conditions, reagents, and starting materials set forth in scheme II.

Scheme II:

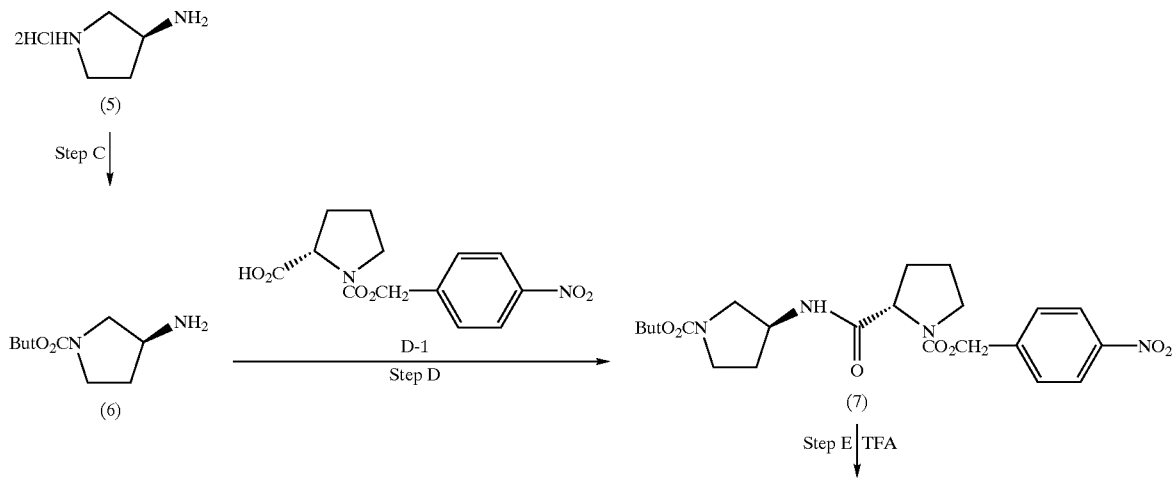

-continued
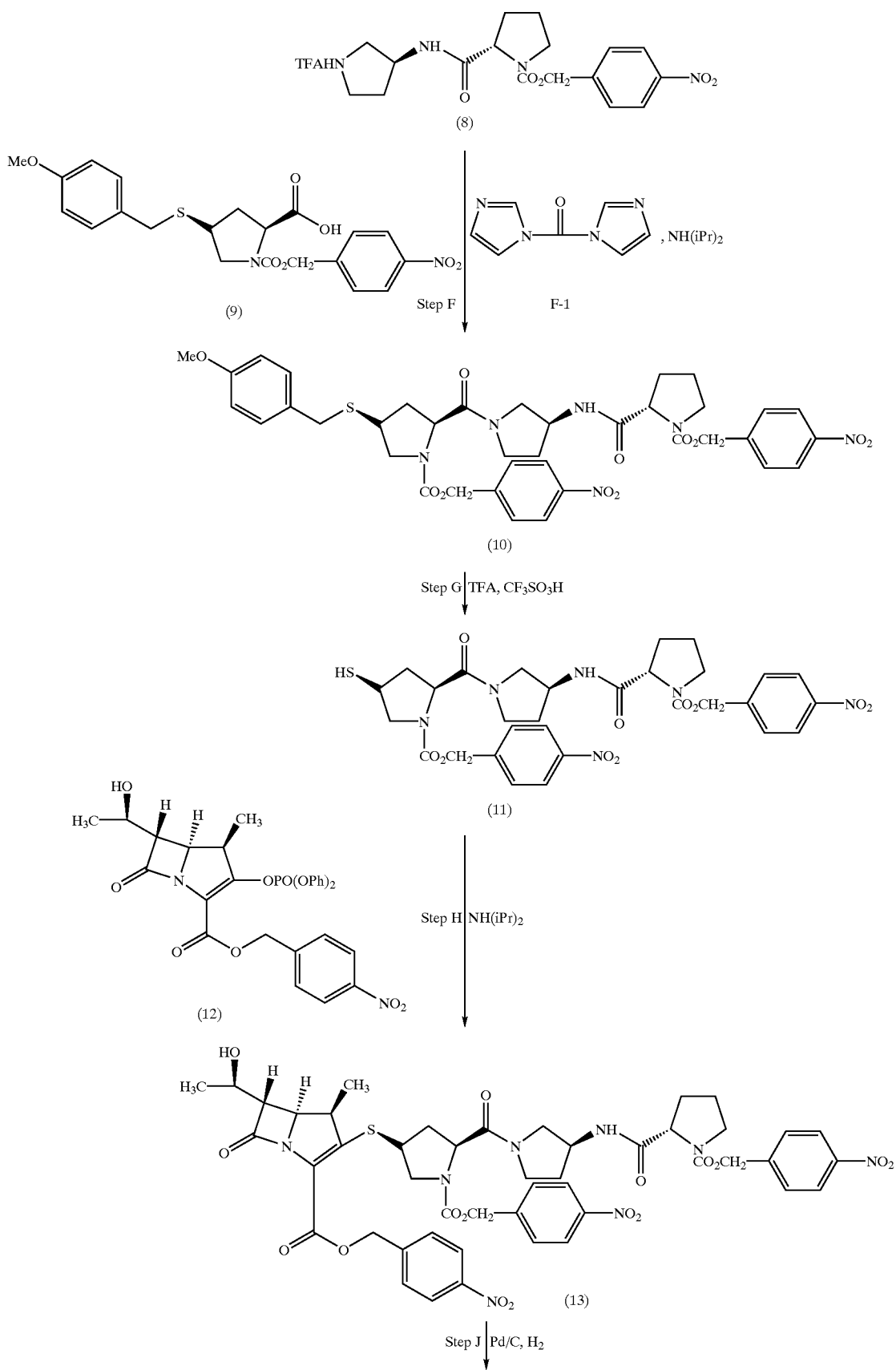

-continued

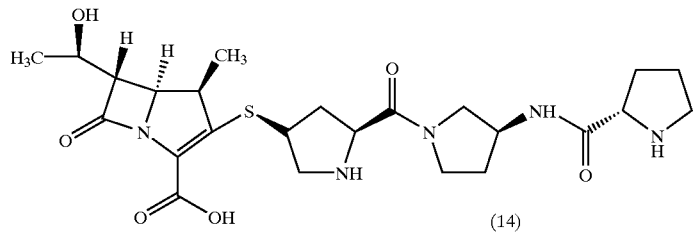

(14)

The optically active 1H-3-aminopyrrolidine compound (5) is reacted with a base and di-tert-butyl carbonate in t-butanol solvent to obtain a compound (6). Examples of the base include inorganic bases such as sodium hydroxide and potassium hydroxide and organic tertiary amines such as triethylamine, trimethylamine, and isopropylamine. Preferred are inorganic bases such as sodium hydroxide and potassium hydroxide. The compound (6) may be purified according to need by silica gel column chromatography, crystallization, etc. (step C).

Steps D to H can be carried out by the method described in Japanese Patent 2955276, which is incorporated herein by reference. Namely, the optically active compound (6) obtained in step (C) is subjected to condensation reaction with 1-(4-nitrobenzyloxycarbonyl)-L-proline (compound D-1) in acetonitrile solvent in the presence of N,N-carbonyldiimidazole to thereby obtain a compound (7) (step D).

Compound (7) is reacted with trifluoroacetic acid in dichloromethane solvent to thereby obtain compound (8) which is a pyrrolidine trifluoroacetate (step E).

Compound (8) and compound (9) are subjected to condensation reaction using a condensation agent (compound (F-1)) in acetonitrile solvent to thereby obtain compound (10) (step F).

Compound (10) is subjected to benzyl elimination in anisole, trifluoroacetic acid, and trifluoromethanesulfonic acid to thereby obtain compound (11) (step G).

Compound (11) and compound (12) are subjected to condensation reaction in acetonitrile solvent using diisopropylamine to thereby obtain compound (13) (step H).

In a solution in tetrahydrofuran/water, compound (13) is hydrogenated using a palladium/carbon catalyst to eliminate the protective groups from the compound (13). Thus, (1R, 5S,6S)-6-[(1R)-1-hydroxyethyl]-1-methyl-2-[(2S,4S)-2-[(3S)-3-(L-amino)pyrrolidin-1-ylcarbonyl]pyrrolidin-4-ylthio]-1-carbapen-2-em-3-carboxylic acid (14) can be obtained (step J).

Furthermore, psychotropic N-3-pyorrolidinyl) benzamide derivatives represented by the following formula (II):

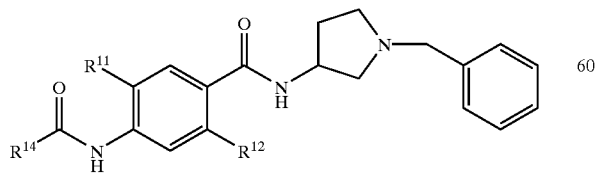

(II)

wherein $R^{11}$ represents a halogen atom; $R^{12}$ represents an alkoxy group having from 1 to 3 carbon atoms; $R^{14}$ represents a hydrocarbon ring group having from 3 to 6 carbon atoms which may be unsubstituted or substituted by halogen atom, which are useful as psychotropic agents, can be synthesized by using the optically active aminopylrrolidine compounds produced by the present method.

In the general formula (II), $R^{11}$ is a halogen atom such as fluorine and chlorine; $R^{12}$ is an alkoxy group having from 1 to 3 carbon atoms such as methoxy, ethoxy, propoxy and iso-propoxy; and $R^{14}$ represents a hydrocarbon ring group having from 3 to 6 carbon atoms which may be unsubstituted or substituted by halogen atom such as cyclopropyl, cyclobutyl, cyclohexyl, phenyl, 2-fluorocyclopropyl, and 2,2-difluorocyclopropyl.

The above mentioned N-(3-pyorrolidinyl) benzamide derivatives can be produced from the compound of formula (4) by the method described in WO95/08533, which is incorporated herein by reference.

As an example of the method of producing the above mentioned N-(3-pyorrolidinyl) benzamide derivatives, the reaction for producing (S)-N-(1-benzyl-3-pyrolidinyl)-5-chloro-4-(cyclopropylcarbonylamino)-2-methoxybenzamido by using an optical active 3-aminoprolidine compound is described in reaction scheme III. However, it is to be understood that the remaining compounds of formula (II) may be prepared by varying the specific conditions, reagents, and starting materials set forth in scheme III.

Scheme III:

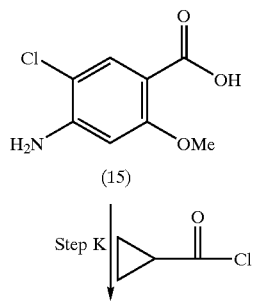

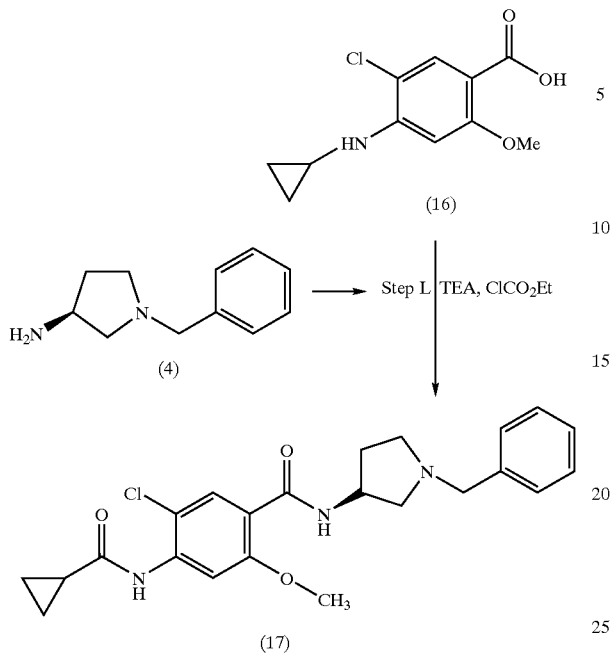

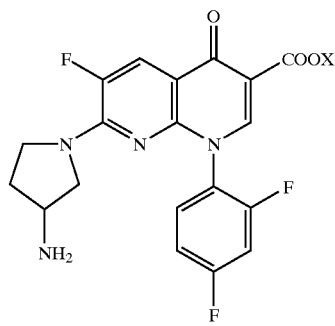

(III)

wherein X is hydrogen or a carboxy protecting group and pharmaceutically acceptable salts thereof, which are useful as antimicrobials. Suitable carboxy protecting groups are disclosed in U.S. Pat. Nos. 3,840,556 and 3,719,667 and EP 0 302 372, which are incorpoarated by reference herein in their entireties. Specifically, the compound of formula (4) may be converted to 3-acetomidopyrrolidine by first converting the 3-amino group of the compound of formula (4) to a 3-acetomido group by reaction of compound (4) with acetic anhydride, followed by removal of the R' protecting group by catalytic hydrongenolysis. The conversion of 3-acetomidopyrrolidine to the compounds of formula (III) may be carried out as described in EP 0 302 372, which, as noted above, is incorpoarated by reference herein in its entirety.

Steps K and L can be carried out by the method described in WO 95/08533 (AU 7665694). Namely, compound (15) is reacted with cyclopropionyl chloride in methylene chloride solvent in the presence of pyridine to thereby obtain compound (16) (step K).

Subsequently, compound (16) is condensed with the optically active 1H-3-aminopyrrolidine compound (4) using triethylamine (TEA) and ethyl chloroformate. Thus, (S)-N-(1-benzyl-3-pyrrolidinyl)-5-chloro-4-(cyclopropyl-carbonylamino)-2-methoxybenzamide (17) can be obtained (step L).

As also noted above, the compound of formula (4) prepared by the present process are useful for preparing the compounds of formula (III):

The invention will be explained below in more detail by reference to Examples. However, the invention should not be construed as being limited to the following Examples unless the invention departs from the spirit thereof.

EXAMPLES

In the following examples, and throughout this specification, all parts and percentages are by weight, and all temperatures are in degrees Celsius, unless expressly stated to be otherwise.

The reaction paths shown in scheme IV were used.

Scheme IV:

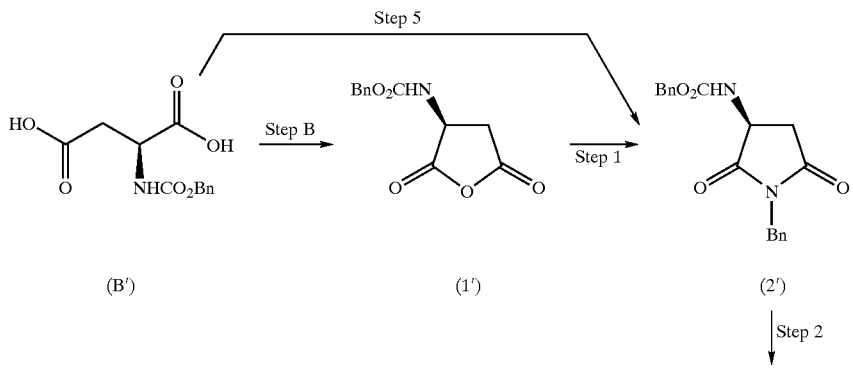

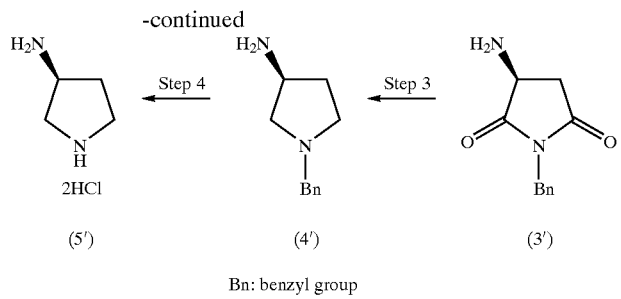

Bn: benzyl group

The structures of reaction products were ascertained by $^1$H-NMR spectroscopy (CDCl$_3$), and the chemical purities thereof were determined by high-performance liquid chromatography (hereinafter abbreviated as HPLC) or gas chromatography (hereinafter abbreviated as GC). With respect to optical purity, each reaction product was analyzed by high-performance liquid chromatography with a column for separating optical isomers and the optical purity thereof was calculated as percentage of excess enantiomer (%ee). HPLC conditions for determining optical purity are as follows.

The optically active amino-protected aspartic acid used in the Examples was a commercially available one or one synthesized from an optically active aspartic acid by the method described above.

Analysis of N-benzyloxycarbonyl-L-aspartic acid:
Column: Chiralpak AD
Eluent: n-Hexane/2-propanol/formic acid=80/20/1
Flow rate: 0.5 mL/min·· (The unit "L" as used herein means "liter".)
Detection wavelength: 254 nm
Analysis of (3S)-1-benzyl-3-benzyloxycarbonyl-aminopyrrolidine-2,5-dione:
Column: Chiralpak AD
Eluent: n-Hexane/2-propanol/formic acid=80/20/1
Flow rate: 0.5 mL/min
Detection wavelength: 254 nm
Analysis of (3S)-1-benzyl-3-aminopyrrolidine-2,5-dione:
Column: CROWNPAK CR (+)
Eluent: Aqueous perchloric acid solution (pH 2)/methanol=9/1
Flow rate: 0.6 mL/min
Detection wavelength: 210 nm
Analysis of (3S)-1-benzyl-3-aminopyrrolidine:
Column: Chiralcel WH
Eluent: Aqueous copper sulfate solution (0.5 mM)/methanol=70/30
Flow rate: 0.6 mL/min
Detection wavelength: 254 nm
Analysis of (3S)-1H-3-aminopyrrolidine dihydrochloride:
Column: SUMICHIRAL OA-6100
Eluent: Aqueous copper sulfate solution (0.5 mM)
Flow rate: 1 mL/min
HPLC and GC conditions for determining chemical purity are as follows:
Analysis of (3S)-1-benzyl-3-benzyloxycarbonyl-aminopyrrolidine-2,5-dione (HPLC):
Column: Mightysil RP-18 GP
Eluent: Water/acetonitrile/trifluoroacetic acid=500/300/0.8
Flow rate: 1.0 mL/min
Detection wavelength: 210 nm
Analysis of (3S)-3-amino-1-benzylpyrrolidine (GC):
Column: NEUTRABOND-1
Column temperature: 100–250° C. (heating rate: 10° C./min)
Carrier gas: Helium (17.7 mL/min)
Chemical purity by HPLC (%)=percentage by area of the target compound (%):
Percentage of excess enantiomer (%ee)=100×{(number of moles of the target compound of one configuration)−(number of moles of the target compound of the other configuration)}/{(number of moles of the target compound of one configuration)+(number of moles of the target compound of the other configuration)}

Example 1

(Step B): Production of N-Benzyloxycarbonyl-L-aspartic Anhydride (Compound 1')

In 80.0 mL of ethyl acetate was suspended 20.1 g (75.2 mmol) of N-benzyloxycarbonyl-L-aspartic acid (compound B'). This solution was stirred at 10° C. in a nitrogen atmosphere. Thereto was added dropwise 17.7 g of acetyl chloride (98%, 221.0 mmol) at 10 to 15° C. The resultant mixture was stirred at room temperature for 1 hour and then at 60° C. for 2 hours. After completion of the reaction, the solvent and the excess acetyl chloride were removed by distillation under reduced pressure. To the residue was added 121 mL of heptane to cause crystallization. These crystals were isolated by filtration, washed, and then vacuum-dried to obtain 18.7 g (75.1 mmol) of white crystals. The solid obtained was ascertained to be N-benzyloxycarbonyl-L-aspartic anhydride (compound 1') by $^1$H-NMR spectroscopy. This compound was converted through hydrolysis into N-benzyloxycarbonyl-L-aspartic acid, which was analyzed by HPLC. As a result, the optical purity of the target compound obtained was found to be 100%ee.

Example 2

(Step 1): Production of (3S)-1-Benzyl-3-benzyloxycarbonylaminopyrrolidine-2,5-dione (Compound 2')

In a mixture of 240 mL of toluene and 26 mL of dimethylformamide was dissolved 21.9 g of the N-benzyloxycarbonyl-L-aspartic anhydride (compound 1') obtained in step B. Thereto was added dropwise 8.1 g (75.2 mmol) of benzylamine at 30 to 40° C. The resultant mixture was heated with refluxing for 1 hour. This reaction mixture was cooled to 30 to 40° C., and 1.4 g (7.5 mmol) of p-toluenesulfonic acid monohydrate was added thereto. Thereafter, a Dean Stark condenser was attached to the reactor, and the reaction mixture was heated at 110° C. with stirring and refluxing for 24 hours to conduct dehydration and then cooled. Thereto was added 350 mL of ethyl acetate. This mixture was subjected three times to washing with 180 mL of saturated aqueous sodium chloride solution, followed by liquid separation each time. The ethyl acetate solution was dried and then concentrated to 50 mL. The crystals precipitated were isolated by vacuum filtration and washed three times with 50 mL of hexane. Thus, 19.7 g of crystals were obtained. The crystals obtained were ascertained to be (3S)-1-benzyl-3-benzyloxycarbonylaminopyrrolidine-2,5-dione (compound 2') by $^1$H-NMR spectroscopy. Analysis by HPLC revealed that this reaction product had a chemical purity of 99.0% and an optical purity of 100%ee.

Example 3
(Step 1): Production of (3S)-1-Benzyl-3-benzyloxycarbonylaminopyrrolidine-2,5-dione (Compound 2')

In a mixture of 980 mL of toluene and 126 mL of dimethylformamide was dissolved 97.81 g (392.81 mmol) of N-benzyloxycarbonyl-L-aspartic anhydride (compound 1'). Thereto was added dropwise 42.03 g (392.81 mmol) of benzylamine at 22 to 33° C. Thereafter, a Dean Stark condenser was attached to the reactor, and the reaction mixture was heated with refluxing and stirring for 1 hour and then cooled. Thereto was added 7.46 g (39.26 mmol) of p-toluenesulfonic acid monohydrate. This mixture was heated at 110° C. with refluxing for 30 hours to conduct azeotropic dehydration (reaction yield, 77%; optical purity, 96%ee). After completion of the reaction, the reaction mixture, while being kept at 70° C., was subjected twice to washing with 140 mL of saturated aqueous sodium hydrogen carbonate solution and then once to washing with 70 mL of saturated aqueous sodium chloride solution, followed by liquid separation each time. Subsequently, the organic layer obtained was heated with refluxing for 30 minutes to conduct azeotropic dehydration and then cooled to cause crystallization. Crystals began to separate out at 65° C. This organic layer was stirred for 1 hour with cooling from 65 to 20° C. and then further stirred at 10° C. or lower for 30 minutes. The crystals formed were isolated by filtration, washed with 150 mL of toluene, and then vacuum-dried to obtain 75.91 g of white crystals (224.59 mmol; isolation yield, 57.2%). The solid obtained was ascertained to be (3S)-1-benzyl-3-benzyloxycarbonylaminopyrrolidine-2,5-dione (compound 2') by $^1$H-NMR spectroscopy. Analysis by HPLC revealed that this reaction product had a chemical purity of 100% and an optical purity of 99.6%ee.

Example 4
(Step 5): Production of (3S)-1-Benzyl-3-benzyloxycarbonylaminopyrrolidine-2,5-dione (Compound 2')

In 15 mL of ethyl acetate was suspended 5.0 g (18.73 mmol) of N-benzyloxycarbonyl-L-aspartic acid (compound B'). This solution was stirred at room temperature in a nitrogen atmosphere. Thereto was added dropwise 1.76 g of acetyl chloride (98%, 22.48 mmol). The mixture was stirred at 60° C. for 2 hours. After completion of the reaction, 50 mL of toluene and 6 mL of dimethylformamide were added to the reaction mixture. The resultant mixture was heated to 90 to 103° C. to remove 20 mL of volatile ingredients including the ethyl acetate and the excess acetyl chloride by azeotropic distillation. The N-benzyloxycarbonyl-L-aspartic anhydride (compound 1) thus yielded was subjected to the subsequent step without being taken out. To the reaction mixture was added dropwise 2.0 g (18.69 mmol) of benzylamine at 44 to 54° C. Thereafter, a Dean Stark condenser was attached to the reactor, and the reaction mixture was heated with refluxing and stirring for 30 minutes. After the reaction mixture was cooled, 0.36 g (18.95 mmol) of p-toluenesulfonic acid monohydrate was added thereto and this mixture was heated at 110° C. with refluxing for 8 hours to conduct azeotropic dehydration (reaction yield, 80%; optical purity, 94%ee). The resultant reaction mixture was cooled and then, while being kept at 70° C., subjected twice to washing with 10 mL of saturated aqueous sodium hydrogen carbonate solution and then once to washing with 10 mL of saturated aqueous sodium chloride solution, followed by liquid separation each time. Subsequently, the organic layer obtained was heated with refluxing for 30 minutes to conduct azeotropic dehydration and then cooled to cause crystallization. Crystals began to separate out at 65° C. The organic layer was stirred for 1 hour with cooling to 20° C. and then further stirred at 10° C. or lower for 30 minutes. The crystals formed were isolated by filtration, washed with 20 mL of toluene, and then vacuum-dried to obtain 4.64 g of white crystals (13.73 mmol; isolation yield, 71.1%). The solid obtained was ascertained to be (3S)-1-benzyl-3-benzyloxycarbonylaminopyrrolidine-2,5-dione (compound 2') by $^1$H-NMR spectroscopy. Analysis by HPLC revealed that this reaction product had a chemical purity of 100% and an optical purity of 100%ee.

Example 5
Purification of (3S)-1-Benzyl-3-benzyloxycarbonylaminopyrrolidine-2,5-dione (Compound 2')

To 69.7 mL of toluene was added 13.94 g of (3S)-1-benzyl-3-benzyloxycarbonylaminopyrrolidine-2,5-dione (compound 2') (optical purity, 92.9%ee). This mixture was heated to 80° C. to completely dissolve the solid and then cooled to cause crystallization. Crystals began to separate out at 65° C., and stirring was continued for 1 hour with cooling to 20° C. The crystals formed were taken out by filtration, washed with 70 mL of toluene, and then vacuum-dried to obtain 13.10 g of white crystals (recovery, 94.0%). Analysis by HPLC revealed that the compound recovered had a chemical purity of 100% and an optical purity of 100%ee.

Example 6
(Step 2): Production of (3S)-3-Amino-1-benzylpyrrolidine-2,5-dione (Compound 3')

In 400 mL of ethanol was dissolved 6.76 g (20 mmol) of (3S)-3-benzyloxycarbonylamino-1-benzyl-pyrrolidine-2,5-dione (compound 2') with heating (40° C.). Thereto was added 53 mg (0.05 mmol) of 10% Pd/C. This mixture was stirred at 20 to 25° C. for 12 hours in a hydrogen atmosphere having ordinary pressure. After completion of the reaction, the catalyst was removed by filtration and the ethanol was removed by distillation under reduced pressure. The residue was vacuum-dried to obtain 4.1 g of an oily substance. The oily substance obtained was ascertained to be (3S)-3-amino-1-benzylpyrrolidine-2,5-dione (compound 3'; yield, 91%) by $^1$H-NMR spectroscopy.

Example 7
(Step 2): Production of (3S)-3-Amino-1-benzylpyrrolidine-2,5-dione (Compound 3')

In 1,220 mL of ethanol was dissolved 113.08 g of (3S)-3-benzyloxycarbonylamino-1-benzylpyrrolidine-2,5-dione (compound 2') (334.56 mmol; optical purity, 99.5%ee). Thereto was added 1.78 g (0.84 mmol) of 5% Pd/C. This mixture was stirred at 20 to 24° C. for 34 hours in a hydrogen atmosphere having ordinary pressure (optical purity, 98.9%ee). After completion of the reaction, the catalyst was separated from the reaction mixture by filtration and washed with 60 mL of ethanol. From the filtrate was removed 1,130 mL of the solvent by vacuum distillation (liquid temperature, 20 to 32° C.). To the residue was added 600 mL of heptane to cause crystallization. The crystals formed were taken out by filtration, washed with 100 mL of heptane, and then vacuum-dried to obtain 63.82 g of white crystals (312.8 mmol; isolation yield, 93.5%). The crystals obtained were ascertained to be (3S)-3-amino-1-benzylpyrrolidine-2,5-dione (compound 3') by $^1$H-NMR spectroscopy. Analyses by GC and HPLC revealed that this reaction product had a chemical purity of 100% and an optical purity of 98.2%ee, respectively.

Example 8
(Step 3): Production of (3S)-3-Amino-1-benzylpyrrolidine (Compound 4')

In a nitrogen stream, 4.68 g of sodium boron hydride (95%; 117.6 mmol) was stirred in 72 mL of tetrahydrofuran, and 15.6 g of dimethyl sulfate (95%; 117.6 mmol) was added dropwise thereto at a liquid temperature of 7 to 14° C. Thereafter, the mixture was reacted with stirring at 14 to 24° C. for 4 hours. After completion of gas evolution, a solution of 6.0 g of (3S)-3-amino-1-benzylpyrrolidine-2,5-dione (compound 3') (29.41 mmol; optical purity, 99.5%ee) in 18 mL of tetrahydrofuran was added dropwise to the reaction mixture at 9 to 15° C., and this mixture was stirred at room temperature for 19 hours. Thereto was added 3 mL of water at 7 to 11° C. This reaction mixture was concentrated under reduced pressure, and 5 mL of 35% hydrochloric acid was then added thereto. The resultant mixture was refluxed at an internal temperature of 110° C. for 1 hour and then cooled. Thereto was added 4 g of solid sodium hydroxide (96%). This mixture was stirred, filtered through a Celite, and then extracted with 20 mL of toluene three times. The extract was dried, filtered, and washed with 20 mL of toluene. The solvent was removed by distillation under reduced pressure to obtain 4.82 g (27.4 mmol) of a yellow liquid. The liquid obtained was ascertained to be (3S)-3-amino-1-benzylpyrrolidine (compound 4') by $^1$H-NMR spectroscopy. Analyses by GC and HPLC revealed that this reaction product had a chemical purity of 89.6% and an optical purity of 97.1%ee, respectively.

Example 9
(Step 3): Production of (3S)-3-Amino-1-benzylpyrrolidine (Compound 4')

Into a three-necked flask made of glass having a capacity of 300 mL were introduced in a nitrogen stream 2.3 g (60 mmol) of sodium boron hydride and 50 mL of tetrahydrofuran together with a stirrer. Thereto was added dropwise 7.6 g (60 mmol) of dimethyl sulfate at a liquid temperature of 0 to 5° C. Thereafter, the reaction mixture was stirred at a temperature of 0 to 20° C. for 7 hours. After the completion of gas evolution, a solution of 2.0 g of (3S)-3-amino-1-benzylpyrrolidine-2,5-dione (compound 3') (10 mmol; optical purity, 99.5%ee) in 8 mL of tetrahydrofuran was added dropwise to the reaction mixture at 0 to 5° C., and this mixture was stirred at 20 to 30° C. for two hours and then at 50° C. for 5 hours. Thereto was added 5 mL of water with cooling with ice. The tetrahydrofuran was removed by distillation under reduced pressure. To the residue was added 40 mL of 6 N hydrochloric acid at room temperature. This mixture was stirred at 20 to 25° C. for 18 hours, and the white solid precipitated was isolated by vacuum filtration and washed twice with 20 mL of chloroform. The chloroform contained in the resultant solution was removed by distillation under reduced pressure, and 60 mL of 20% by weight aqueous sodium hydroxide solution was added to the residue to give a solution having a pH of 13. This solution was extracted with chloroform (100 mL×2). The extract was dried and the solvent was then removed by distillation under reduced pressure to obtain 1.4 g of a liquid (yield, 80%). The liquid obtained was ascertained to be (3S)-3-amino-1-benzylpyrrolidine (compound 4') by $^1$H-NMR spectroscopy. Analyses by GC and HPLC revealed that this reaction product had a chemical purity of 94.7% and an optical purity of 100%ee, respectively.

Example 10.
(Steps 2 and 3): Production of (3S)-3-Amino-1-benzylpyrrolidine (Compound 4)

In 300 mL of 1,2-dimethoxyethane was dissolved 75.27 g of (3S)-3-benzyloxycarbonylamino-1-benzyl-pyrrolidine-2, 5-dione (229.69 mmol; optical purity, 99.6%ee). Thereto was added 1.18 g (0.57 mmol) of 5% Pd/C. This mixture was stirred at 22 to 26° C. for 25 hours in a hydrogen atmosphere having ordinary pressure (optical purity, 100%ee). After completion of the reaction, the catalyst was separated from the reaction mixture by filtration and washed with 50 mL of 1,2-dimethoxyethane. The residual solution was subjected to the following step without removing the (3S)-3-amino-1-benzylpyrrolidine-2,5-dione (compound 3') from the reaction vessel.

Subsequently, 26.6 g of sodium boron hydride (95%; 668 mmol) and 230 mL of dimethoxyethane were introduced into a reactor at room temperature in a nitrogen stream. Thereto was added 29.72 g (222.7 mmol) of aluminum chloride h stirring at a liquid temperature of 10 to 30° C. This mixture was stirred at 40° C. for 30 minutes. Subsequently, the 1,2-dimethoxyethane solution of (3S)-3-amino-1-benzylpyrrolidine-2,5-dione (compound 3') prepared above was added dropwise to the mixture at 4 to 7° C. The resultant mixture was reacted first at 23 to 27° C. for 16.5 hours and then at 30° C. for 1.5 hours. To this reaction mixture was added 180 mL of water at 12 to 17° C. The resultant mixture was concentrated at 70 to 86° C. under reduced pressure to remove 585 mL of the solvent by distillation. After the concentration, 139.34 g (1,336.14 mmol) of 35% hydrochloric acid was added to the concentrate, and this mixture was refluxed for 1 hour at an internal temperature of 65 to 78° C. and then cooled. Thereto was added 111.33 g of solid sodium hydroxide (96%; 2,672 mmol). This mixture was filtered through a Celite and then subjected to extraction with 200 mL of toluene, followed by liquid separation. The aqueous layer was further subjected to extraction with 100 mL of toluene, followed by liquid separation. The toluene layer collected was heated with refluxing to conduct azeotropic dehydration for 20 minutes. Thereafter, the solvent was removed by distillation under reduced pressure to obtain 39.58 g of a yellow liquid (yield, 90.5%). The liquid obtained was ascertained to be (3S)-3-amino-1-benzylpyrrolidine (compound 4') by $^1$H-NMR spectroscopy. Analyses by GC and HPLC revealed that this reaction product had a chemical purity of 89.6% and an optical purity of 99.2%ee, respectively.

Example 11
(Step 4): Production of (3S)-1H-3-aminopyrrolidine Dihydrochloride (Compound 5')

In 270 mL of ethanol was dissolved 38.66 g of (3S)-3-amino-1-benzylpyrrolidine (compound 4') (196.8 mmol; chemical purity, 89.6%). Thereto were added 11.86 g (393.6 mmol) of acetic acid and 1.05 g (0.492 mmol) of 5% Pd/C.

The resultant mixture was stirred at 60 to 70° C. for 6 hours in a hydrogen atmosphere having an elevated pressure of 4.5 kg/cm². After completion of the reaction, the catalyst was taken out by filtration and washed with 116 mL of ethanol. Into the filtrate was bubbled 70 g of hydrogen chloride gas at 10 to 40° C. to cause crystallization. This mixture was further stirred at 5° C. or lower for 30 minutes. The precipitate formed was taken out by filtration, washed with 100 mL of ethanol, and then dried to obtain 28.88 g of crude crystals (yield, 91.9%; chemical purity, 96.7%; optical purity, 99.3%ee). A 28.25 g portion of the crude crystals was weighed out. Thereto were added 300 mL of ethanol and 60 mL of water, followed by 36 g of hydrogen chloride gas. The resultant mixture was heated at 80° C. to completely dissolve the crystals and then cooled. As a result, crystallization began at 75° C. This mixture was aged while being cooled to 0° C. over 2 hours. The crystals formed were isolated by filtration, washed with 100 mL of ethanol, and then vacuum-dried to obtain 23.21 g (146.0 mmol) of white crystals. The crystals obtained were ascertained to be (3S)-1H-3-aminopyrrolidine dihydrochloride (compound 5') by ¹H-NMR spectroscopy and elemental analysis. Analyses by GC and HPLC revealed that this reaction product had a chemical purity of 99.6% and an optical purity of 99.3%ee, respectively.

Comparative Example 1
(Step 1): Production of (3S)-1-Benzyl-3-benzyloxycarbonylaminopyrrolidine-2,5-dione (Compound 2')

In 50 mL of ethanol were suspended 8.0 g of the crude crystals of N-benzyloxycarbonyl-L-aspartic anhydride (compound 1') obtained in Example 1. A solution of 10.3 mL (94 mmol) of benzylamine in 10 mL of ethanol was added dropwise to the suspension. Thereafter, the reaction mixture was stirred at 20° C. for 18 hours and then acidified to a pH of 3 with 1 N HCl solution. The precipitate thus formed was isolated by suction filtration, washed with 25 mL of water three times, and then vacuum-dried to obtain 8.3 g of a white solid. An 8.0 g portion of the solid was suspended in 15 mL of acetic anhydride. This reaction mixture was stirred with heating at 60° C. for 24 hours and then cooled to room temperature. Thereafter, the solvent was removed by distillation under reduced pressure, and the residue was dissolved in 10 mL of dichloromethane. The solution was washed with 50 mL of an aqueous sodium carbonate solution and 50 mL of water and then dried with magnesium sulfate. Thereafter, the solvent was removed by distillation under reduced pressure to obtain 7.2 g of crystals. The crystals obtained were ascertained to be (3S)-1-benzyl-3-benzyloxycarbonylaminopyrrolidine-2,5-dione (compound 2') by ¹H-NMR spectroscopy. Analysis by HPLC revealed that this reaction product had an optical purity of 65%ee.

Comparative Example 2
(Step 3): Production of (3S)-3-Amino-1-benzylpyrrolidine (Compound 4')

Into a three-necked flask made of glass having a capacity of 300 mL were introduced in a nitrogen stream 0.23 g (6.2 mmol) of lithium aluminum hydride and 10 mL of tetrahydrofuran together with a stirrer. A solution of 1.2 g (5.6 mmol) of (3S)-3-amino-1-benzylpyrrolidine-2,5-dione (compound 3') in 5 mL of tetrahydrofuran was added dropwise thereto at a liquid temperature of 0 to 5° C. This mixture was stirred at 20 to 30° C. for 18 hours. To the resultant reaction mixture were added 230 mL of water and 69 mL of 6 N sodium hydroxide solution with cooling with ice. The precipitate formed was removed by vacuum filtration, and the filtrate was washed with 50 mL of ethyl acetate three times. The organic layer was dried with sodium sulfate, and the solvent was then removed by distillation under reduced pressure to obtain 0.86 g of a liquid. The liquid obtained was ascertained to be (3S)-3-amino-1-benzylpyrrolidine (compound 4') by ¹H-NMR spectroscopy. Analysis by HPLC revealed that this reaction product had an optical purity of 97%ee.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

What is claimed is:
1. A process for producing 1H-3-aminopyrrolidine or a protonic acid salt thereof, which comprises:

(a) reacting an amino-protected aspartic anhydride of formula (1):

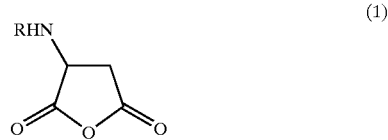

wherein R represents a benzyloxycarbonyl group which may have one or more substituents on the benzene ring,
with a primary amine represented by the formula R'NH₂ wherein R' represents an aralkyl group which may have one or more substituents on the aromatic ring, to obtain a reaction product;

(b) subjecting said reaction product to cyclodehydration to obtain a 1-aralkyl-3-(protected amino)pyrrolidine-2,5-dione compound of formula (2):

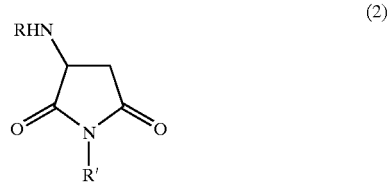

wherein R has the same meaning as in formula (1) and R' is as defined above;

(c) replacing R with a hydrogen at the 3-position amino group of the compound of formula (2) to obtain a 1-aralkyl-3-aminopyrrolidine-2,5-dione compound of formula (3):

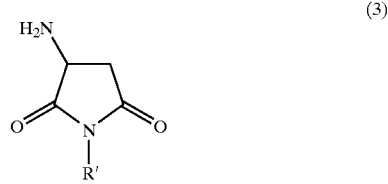

wherein R' has the same meaning as in formula (2);

(d) reducing the carbonyl groups of the compound of formula (3) to obtain either a 1-aralkyl-3-aminopyrrolidine compound of formula (4):

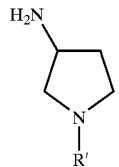

(4)

wherein R' has the same meaning as in formula (2), or a salt thereof with a protonic acid; and (e) subjecting said compound of formula (4) or said salt thereof to hydrogenolysis to obtain 1H-3-aminopyrrolidine or a protonic acid salt thereof.

2. A process for producing optically active 1H-3-aminopyrrolidine or a protonic acid salt thereof, which comprises:

(a) reacting an optically active amino-protected aspartic anhydride of formula (1') or (1''):

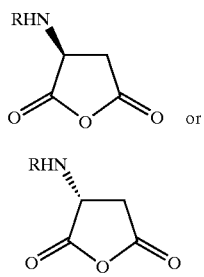

(1')

or (1'')

wherein R represents a benzyloxycarbonyl group which may have one or more substituents on the benzene ring,
with a primary amine represented by the formula $R'NH_2$ wherein R' represents an aralkyl group which may have one or more substituents on the aromatic ring, to obtain a reaction product;

(b) subjecting said reaction product to cyclodehydration to obtain an optically active 1-aralkyl-3-(protected amino)pyrrolidine-2,5-dione compound of formula (2') or (2''):

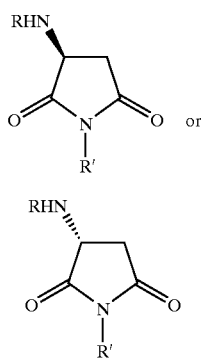

(2')

or (2'')

wherein R has the same meaning as in formula (1') or (1'') and R' is as defined above;

(c) replacing R with a hydrogen at the 3-position amino group of the compound of formula (2') or (2'') to obtain an optically active 1-aralkyl-3-aminopyrrolidine-2,5-dione compound of following formula (3') or (3''):

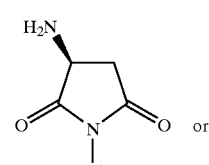

(3')

or (3'')

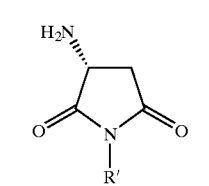

wherein R' has the same meaning as in formula (2') or (2'');

(d) reducing said compound represented by formula (3') or (3'') to obtain either an optically active 1-aralkyl-3-aminopyrrolidine compound of formula (4') or (4''):

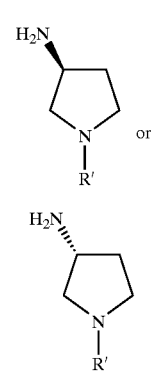

(4')

or (4'')

wherein R' has the same meaning as in formula (2') or (2''), or a salt thereof with a protonic acid; and (e) subjecting the compound of formula (4') or (4'') or said salt thereof to hydrogenolysis to obtain optically active 1H-3-aminopyrrolidine or a protonic acid salt thereof.

3. The process of claim 2, wherein said optically active amino-protected aspartic anhydride is obtained by dehydrating an optically active amino-protected aspartic acid of formula (B) or (B'):

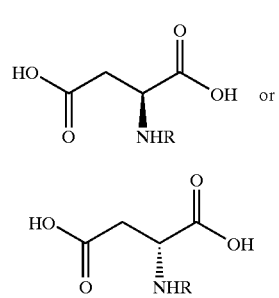

(B)

or (B')

wherein R has the same meaning as in formula (1') or (1'').

4. The process of claim 2, wherein said optically active 1-aralkyl-3-(protected amino)pyrrolidine-2,5-dione compound of formula (2') or (2'') is purified by crystallization.

5. The process of claim 4, wherein said optically active 1-aralkyl-3-(protected amino)pyrrolidine-2,5-dione compound of formula (2') or (2") is purified by crystallization and said crystallization is conducted with an organic solvent comprising an aromatic hydrocarbon.

6. The process of claim 2, wherein said cyclodehydration is conducted in the presence of an acid catalyst.

7. The process of claim 2, wherein said cyclodehydration is conducted in the presence of an acid catalyst and wherein said acid catalyst is a protonic acid.

8. The process of claim 2, wherein said reducing said compound of formula (3') or (3") is conducted in the presence of reducing agent which is prepared by adding dimethyl sulfate or aluminum chloride to sodium boron hydride.

9. A process for producing optically active 1H-3-aminopyrrolidine or a protonic acid salt thereof, which comprises:

(a) a step for obtaining a reaction product of an optically active amino-protected aspartic anhydride of formula (1') or (1"):

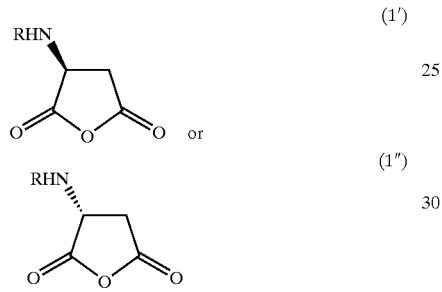

wherein R represents a benzyloxycarbonyl group which may have one or more substituents on the benzene ring,
with a primary amine represented by the formula R'NH₂ wherein R' represents an aralkyl group which may have one or more substituents on the aromatic ring;

(b) or converting said reaction oduct to an optically active 1-aralkyl-3-(protected amino)pyrrolidine-2,5-dione compound of formula (2') or (2"):

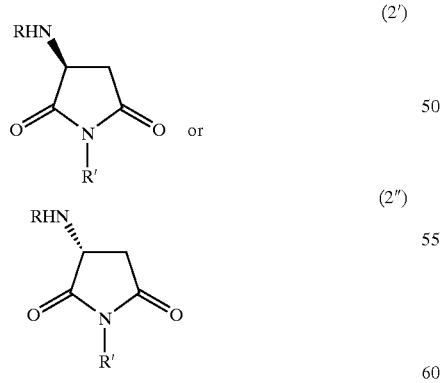

wherein R has the same meaning as in formula (1') or (1") and R' is as defined above;

(c) a step for converting the compound represented by formula (2') or (2") to an optically active 1-aralkyl-3-aminopyrrolidine-2,5-dione compound of formula (3') or (3"):

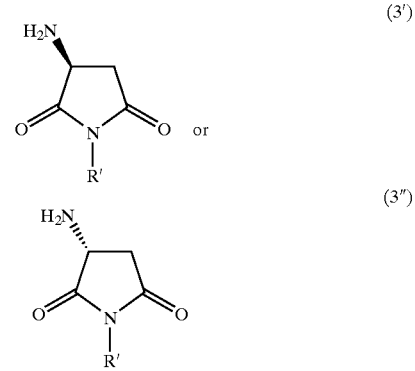

wherein R' has the same meaning as in formula (2') or (2");

(d) a step for converting the compound of formula (3') or (3") to either an optically active 1-aralkyl-3-aminopyrrolidine compound of formula (4') or (4"):

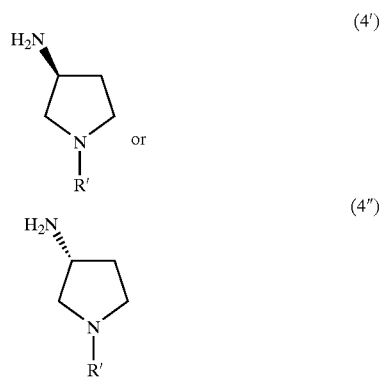

wherein R' has the same meaning as in formula (2') or (2"), or a salt thereof with a protonic acid; and (e) a step for converting the compound of formula (4') or (4") or said salt thereof to hydrogenolysis to obtain optically active 1H-3-aminopyrrolidine or a protonic acid salt thereof.

10. A process for producing an optically active 1-aralkyl-3-(protected amino)pyrrolidine-2,5-dione compound of formula (2') or (2"):

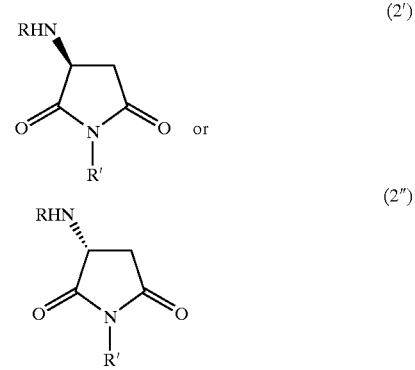

wherein R represents a benzyloxycarbonyl group which may have one or more substituents on the benzene ring; and R' represents an aralkyl group which may have one or more substituents on the aromatic ring, which process comprises:
(a) reacting an optically active amino-protected aspartic anhydride of formula (1') or (1"):

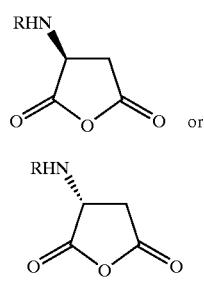

with a primary amine of the formula R'NH$_2$ wherein R and R' are as defined above, to obtain a reaction product; and
(b) subjecting said reaction product to cyclodehydration in the presence of an acid catalyst.

11. The process of claim 10, wherein the optically active amino-protected aspartic anhydride is one obtained by dehydrating an optically active amino-protected aspartic acid of formula (B) or (B'):

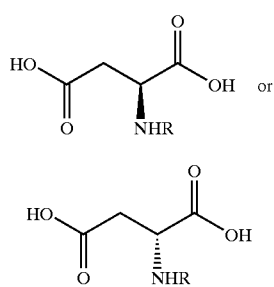

wherein R has the same meaning as in formula (1).

12. The process of claim 10, wherein the optically active 1-aralkyl-3-(protected amino)pyrrolidine-2,5-dione compound of formula (2') or (2") is purified by crystallization.

13. The process of claim 10, wherein said optically active 1-aralkyl-3-(protected amino)pyrrolidine-2,5-dione compound of formula (2') or (2") is purified by crystallization and said crystallization is conducted with an organic solvent comprising an aromatic hydrocarbon.

14. A process for producing an optically active 1-aralkyl-3-(protected amino)pyrrolidine-2,5-dione compound of formula (2') or (2"):

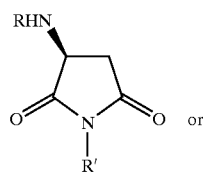

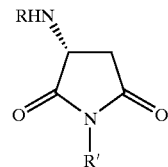

wherein R represents a benzyloxycarbonyl group which may have one or more substituents on the benzene ring; and R' represents an aralkyl group which may have one or more substituents on the aromatic ring,
which process comprises:
(a) dehydrating an optically active amino-protected aspartic acid of formula (B) or (B'):

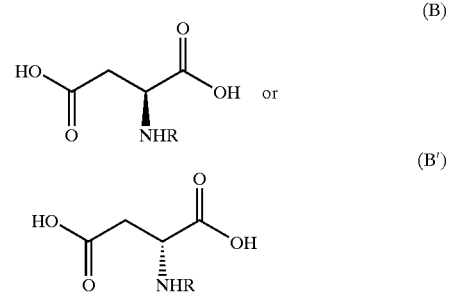

wherein R has the same meaning as in formula (2') or (2"), to obtain an optically active amino-protected aspartic anhydride;
(b) reacting said anhydride with a primary amine of the formula R'NH$_2$ wherein R' represents an aralkyl group which may have one or more substituents on the aromatic ring, to obtain a reaction product; and
(c) subjecting said reaction product to cyclodehydration, wherein said reacting said anhydride and said subjecting said reaction product are carried out in a same reactor without removing said reaction product from said reactor between said reacting said anhydride and said subjecting said reaction product.

15. The process of claim 14, wherein said optically active 1-aralkyl-3-(protected amino)pyrrolidine-2,5-dione compound of formula (2') or (2") is purified by crystallization.

16. The process of claim 14, wherein said optically active 1-aralkyl-3-(protected amino)pyrrolidine-2,5-dione compound of formula (2') or (2") is purified by crystallization and said crystallization is conducted with an organic solvent comprising an aromatic hydrocarbon.

17. The process of claim 14, wherein said cyclodehydration is conducted in the presence of a dehydration catalyst.

18. A process for producing a 1-methyl-carbapenem derivatives represented by the following formula (I):

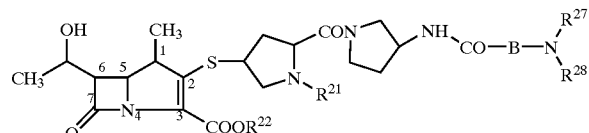

wherein $R^{21}$ represents a hydrogen or methyl group; $R^{22}$ represents hydrogen or an ester residue which is hydrolyzable in vivo; $R^{27}$ represents hydrogen, methyl or ethyl; B represents 1,4-diphenylene, 1,4-cyclohexylenemethyl, methylene, methyl ethylene, ethylene, trimethylene, or 2-hydroxypropylene; $R^{28}$ represents formimidoyl, acetoimidoyl, or amidino; or the group —B—$NR^{27}R^{28}$ represents a 5 or 6 membered heterocyclic group, which process comprises converting 1H-3-aminopyrrolidine or a protonic acid salt thereof to said compound of formula (I), wherein the improvement comprises producing said 1H-3-aminopyrrolidine or a protonic acid salt thereof by a process according to claim 9.

19. A process for producing an optically active 1-aralkyl-3-aminopyrrolidine compound of formula (4') or (4"):

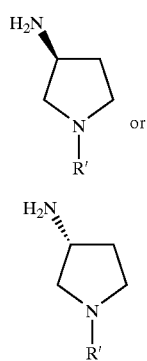

(4')

(4")

wherein R' represents an aralkyl group which may have one or more substituents on the aromatic ring, or a salt thereof with a protonic acid, which process comprises:

(a) reducing an optically active 1-aralkyl-3-aminopyrrolidine-2,5-dione compound of formula (3') or (3"):

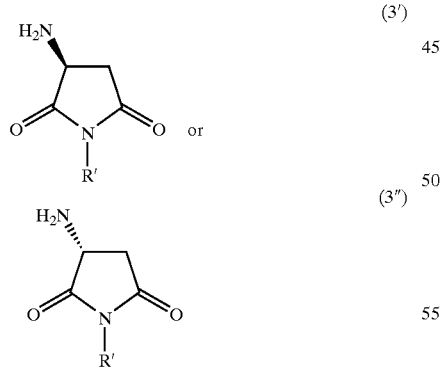

(3')

(3")

wherein R' has the same meaning as in formula (4); with a reducing agent prepared by adding dimethyl sulfate or aluminum chloride to sodium boron hydride.

20. The process of claim 19, wherein said compound of formula (3') or (3") is prepared by replacing R with a hydrogen at the 3-position amino group of the compound of formula (2') or (2"):

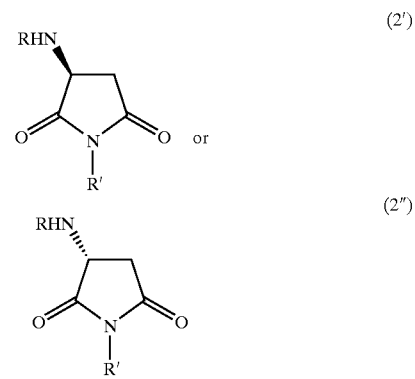

(2')

(2")

wherein R represents a benzyloxycarbonyl group which may have one or more substituents on the benzene ring and R' is as defined above, to obtain said compound of formula (3') or (3").

21. The process of claim 20, wherein said compound represented by formula (2') or (2") is prepared by:

reacting an optically active amino-protected aspartic anhydride of formula (1') or (1"):

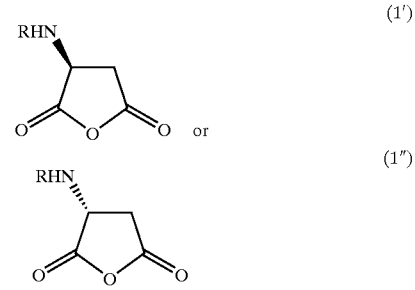

(1')

(1")

wherein R is as defined in formula (2), with a primary amine represented by the formula $R'NH_2$ wherein R' is as defined in formula (3') or (3"), to obtain a reaction product; and subjecting said reaction product to cyclodehydration to obtain said compound of formula (2') or (2").

22. The process of claim 21, wherein said compound of formula (1') or (1") is prepared by:

dehydrating an optically active amino-protected aspartic acid of formula (B) or (B'):

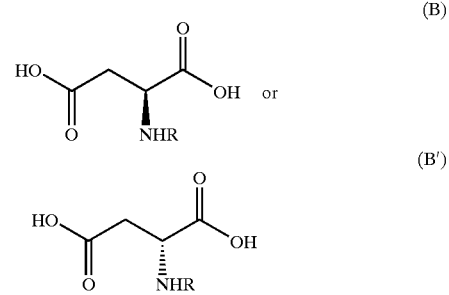

(B)

(B')

wherein R has the same meaning as in formula (1') or (1").

23. A process for producing a 1-methyl-carbapenem derivatives represented by the following formula (I):

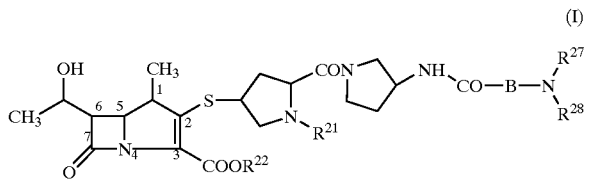

(I)

wherein $R^{21}$ represents a hydrogen or methyl group; $R^{22}$ represents hydrogen or an ester residue which is hydrolyzable in vivo; $R^{27}$ represents hydrogen, methyl or ethyl; B represents 1,4-diphenylene, 1,4-cyclohexylenemethyl, methylene, methyl ethylene, ethylene, trimethylene, or 2-hydroxypropylene; $R^{28}$ represents formimidoyl, acetoimidoyl, or amidino; or the group —B—NR27R28 represents a 5 or 6 membered heterocyclic group, which process comprises converting 1H-3-aminopyrrolidine or a protonic acid salt thereof to said compound of formula (I), wherein the improvement comprises producing said 1H-3-aminopyrrolidine or a protonic acid salt thereof by a process according to claim 1.

24. The process of claim 23, wherein said compound of formula (I) is (1R,5S,6S)-6-[(1R)-1-hydroxyethyl]-1-methyl-2-[(2S,4S)-2-[(3S)-3-(L-prolyl-amino)pyrrolidin-1-ylcarbonyl]pyrrolidin-4-ylthio]-1-carbapen-2-em-3-carboxylic acid.

25. A process for producing a N-(3-pyrolidynyl) benzamido derivative represented by the following formula (II):

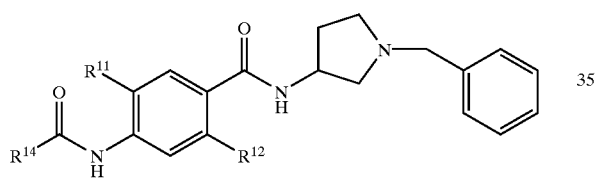

(II)

wherein $R^{11}$ represents a halogen atom; $R^{12}$ represents an alkoxy group having from 1 to 3 carbon atoms; $R^{14}$ represents a hydrocarbon ring group having from 3 to 6 carbon atoms which may be unsubstituted or substituted by halogen atom, which process comprises converting a compound represented by formula (4') or (4"):

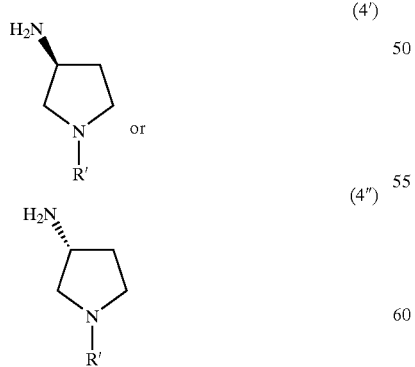

(4')

(4")

wherein R' represents an aralkyl group which may have one or more substituents on the aromatic ring, or a salt thereof with a protonic acid, to said compound of formula (II), wherein the improvement comprises producing said compound represented by formula (4') or (4") by a process according to claim 19.

26. The process of claim 25, wherein said compound of formula (II) is (S)—N-(1-benzyl-3-pyrrolidinyl)-5-chloro-4-(cyclopropylcarbonylamino)-2-methoxybenzamide.

27. A process for producing a N-(3-pyrolidynyl) benzamido derivative represented by the following formula (II):

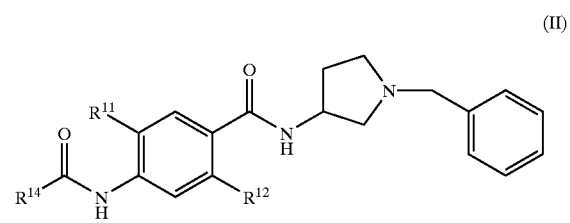

(II)

wherein $R^{11}$ represents a halogen atom; $R^{12}$ represents an alkoxy group having from 1 to 3 carbon atoms; $R^{14}$ represents a hydrocarbon ring group having from 3 to 6 carbon atoms which may be unsubstituted or substituted by halogen atom, which process comprises converting a compound represented by formula (4') or (4"):

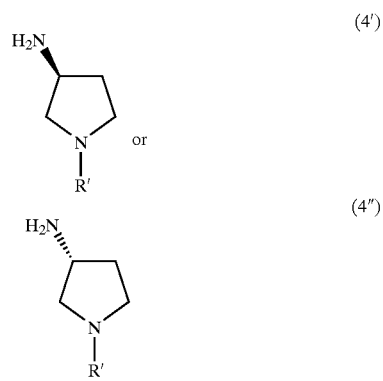

(4')

(4")

wherein R' represents an aralkyl group which may have one or more substituents on the aromatic ring, or a salt thereof with a protonic acid, to said compound of formula (II), wherein the improvement comprises producing said compound represented by formula (4') or (4") by a process which comprises:

(a) reacting an optically active amino-protected aspartic anhydride of formula (1') or (1"):

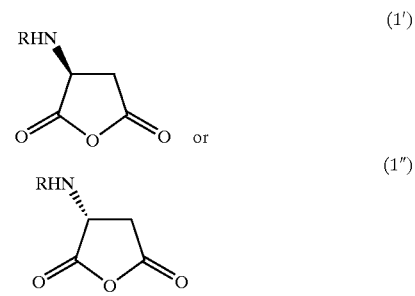

(1')

(1")

wherein R represents a benzyloxycarbonyl group which may have one or more substituents on the benezene ring, with a primary amine represented by the formula R'NH$_2$ wherein R' represents an aralkyl group which may have one or more substituents on the aromatic ring, to obtain a reaction product;

(b) subjecting said reaction product to cyclodehydration in the presence of an acid catalyst to obtain an optically active 1-aralkyl-3-(protected amino) pyrrolidine-2,5-dione compound of formula (2') or (2")

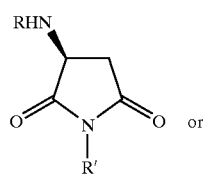

(2')

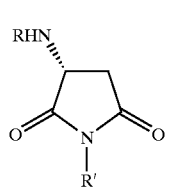

(2")

wherein R has the same meaning as in formula (1') or (1") and R' is as defined above;

(c) replacing R with a hydrogen at the 3-position amino group of the compound of formula (2') or (2") to obtain an optically active 1-aralkyl-3-aminopyrrolidine-2,5-dione compound of following formula (3') or (3"):

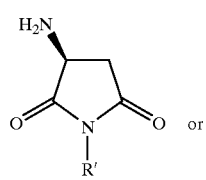

(3')

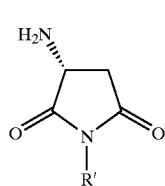

(3")

wherein R' has the same meaning as in formula (2') or (2"); and (d) reducing said compound represented by formula (3') or (3") to obtain said optically active 1-aralkyl-3-aminopyrrolidine compound of formula (4') or (4").

28. A process for producing a compound of formula (III):

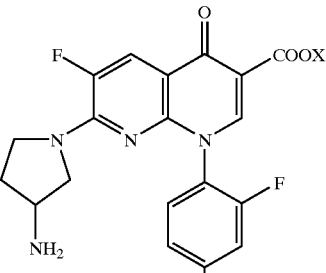

(III)

wherein X is hydrogen or a carboxy protecting group and pharmaceutically acceptable salts thereof, which comprises converting a compound represented by formula (4') or (4"):

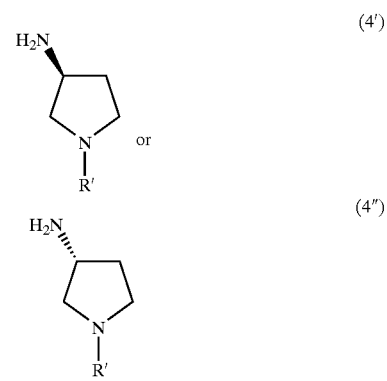

(4')

(4")

wherein R' represents an aralkyl group which may have one or more substituents on the aromatic ring, or a salt thereof with a protonic acid, to said compound of formula (III), wherein the improvement comprises producing said compound represented by formula (4') or (4") by a process according to claim 19.

29. A process for producing a 1-methyl-carbapenem derivatives represented by the following formula (I):

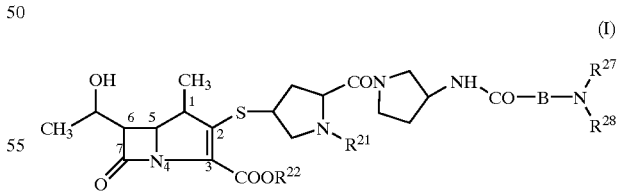

(I)

wherein $R^{21}$ represents a hydrogen or methyl group; $R^{22}$ represents hydrogen or an ester residue which is hydrolyzable in vivo; $R^{27}$ represents hydrogen, methyl or ethyl; B represents 1,4-diphenylene, 1,4-cyclohexylenemethyl, methylene, methyl ethylene, ethylene, trimethylene, or 2-hydroxypropylene; $R^{28}$ represents formimidoyl, acetoimidoyl, or amidino; or the group —B—NR$^{27}$R$^{28}$ represents a 5 or 6 membered heterocyclic group, which process comprises converting 1H-3-aminopyrrolidine or a protonic acid salt thereof to said compound of formula (I), wherein the improvement comprises producing said 1H-3-aminopyrrolidine or a protonic acid salt thereof by a process according to claim 2.

30. The process of claim 29, wherein said compound of formula (I) is (1R,5S,6S)-6-[(1R)-1-hydroxyethyl]-1-methyl-2-[(2S,4S)-2-[(3S)-3-(L-prolyl-amino)pyrrolidin-1-ylcarbonyl]pyrrolidin-4-ylthio]-1-carbapen-2-em-3-carboxylic acid.

31. The process of claim 8, wherein said compound of formula (I) is (1R,5S,6S)-6-[(1R)-1-hydroxyethyl]-1-methyl-2-[(2S,4S)-2-[(3S)-3-(L-prolyl-amino)pyrrolidin-1-ylcarbonyl]pyrrolidin-4-ylthio]-1-carbapen-2-em-3-carboxylic acid.

* * * * *